US008034109B2

(12) United States Patent
Zwirkoski

(10) Patent No.: US 8,034,109 B2
(45) Date of Patent: Oct. 11, 2011

(54) LINKED SLIDEABLE AND INTERLOCKABLE ROTATABLE COMPONENTS

(75) Inventor: Paul Zwirkoski, Brighton, MI (US)

(73) Assignee: Morphogeny, LLC, Pinckney, MI (US)

( * ) Notice: Subject to any disclaimer, the term of this patent is extended or adjusted under 35 U.S.C. 154(b) by 1568 days.

(21) Appl. No.: 11/276,345

(22) Filed: Feb. 24, 2006

(65) Prior Publication Data

US 2006/0189999 A1    Aug. 24, 2006

Related U.S. Application Data

(60) Provisional application No. 60/656,029, filed on Feb. 24, 2005.

(51) Int. Cl.
*A61F 2/44* (2006.01)
*A61B 17/70* (2006.01)
*A61F 2/46* (2006.01)

(52) U.S. Cl. ............... 623/17.11; 623/17.16; 606/86 R; 606/99; 606/90

(58) Field of Classification Search .... 623/17.11–17.16; 606/86 A, 86 B, 86 R, 87–90, 279, 232
See application file for complete search history.

(56) References Cited

U.S. PATENT DOCUMENTS

| | | | |
|---|---|---|---|
| 3,780,400 A | 12/1973 | Hinsperger | 24/16 PB |
| 3,846,846 A | 11/1974 | Fischer | 3/1 |
| 4,038,703 A | 8/1977 | Bokros | 3/1.5 |
| 4,566,832 A | 1/1986 | Mirsberger et al. | 411/21 |
| 4,697,582 A | 10/1987 | William | |
| 4,719,905 A | 1/1988 | Steffee | |
| 4,771,767 A | 9/1988 | Steffee | |
| 4,863,476 A | 9/1989 | Shepperd | |
| 5,059,193 A | 10/1991 | Kuslich | |
| 5,092,866 A | 3/1992 | Breard et al. | |
| 5,372,146 A | 12/1994 | Branch | 128/898 |
| 5,390,683 A | 2/1995 | Pisharodi | |

(Continued)

FOREIGN PATENT DOCUMENTS

DE       197 10392 C1     7/1999

(Continued)

OTHER PUBLICATIONS

Supplementary Partial European Search Report for Application No. EP 06736059.4, dated Jun. 17, 2009.

(Continued)

*Primary Examiner* — Thomas C. Barrett
*Assistant Examiner* — Matthew Lawson
(74) *Attorney, Agent, or Firm* — Marshall, Gerstein & Borun LLP

(57) ABSTRACT

Medical devices having one or more rotatable linkable components or segments, delivered in a first orientation relative to a component guide into a tissue cavity, such as the interbody vertebral space. After delivery, each segment may be rotated to a second, different orientation relative to the component guide, such as into a permanent vertical standing position. The segments achieve maximum distraction of the cavity space such as adjacent vertebra end plates, while using a minimal invasive surgical (MIS) approach. When the segments are tightened in place, the device provides long-term stability. The device can be used as a distraction instrument and/or permanent implant that can be used for interbody fusion, nuclear replacement, or anywhere in the body where a stable distraction of tissue and/or the implantation of material such as a device with an MIS approach is desired.

13 Claims, 28 Drawing Sheets

U.S. PATENT DOCUMENTS

| | | | | |
|---|---|---|---|---|
| 5,405,359 | A | * | 4/1995 | Pierce ............................ 606/232 |
| 5,443,514 | A | | 8/1995 | Steffee |
| 5,505,736 | A | | 4/1996 | Reimels et al. ................. 606/72 |
| 5,520,691 | A | | 5/1996 | Branch ........................... 606/72 |
| 5,601,556 | A | | 2/1997 | Pisharodi |
| 5,672,175 | A | | 9/1997 | Martin |
| 5,702,454 | A | | 12/1997 | Baumgartner ................... 623/17 |
| 5,756,127 | A | | 5/1998 | Grisoni et al. .................. 424/489 |
| 5,769,898 | A | | 6/1998 | Jisander ........................... 623/16 |
| 5,904,682 | A | | 5/1999 | Rogozinski |
| 5,989,291 | A | | 11/1999 | Ralph et al. |
| 6,102,934 | A | * | 8/2000 | Li ................................. 606/232 |
| 6,102,950 | A | | 8/2000 | Vaccaro |
| 6,126,689 | A | | 10/2000 | Brett |
| 6,296,644 | B1 | | 10/2001 | Saurat et al. |
| 6,387,130 | B1 | * | 5/2002 | Stone et al. ................. 623/17.16 |
| 6,595,998 | B2 | | 7/2003 | Johnson et al. ................. 606/90 |
| 6,695,842 | B2 | | 2/2004 | Zucherman et al. |
| 6,706,044 | B2 | | 3/2004 | Kuslich et al. |
| 6,936,071 | B1 | | 8/2005 | Marnay et al. ............. 623/17.15 |
| 6,986,771 | B2 | | 1/2006 | Paul et al. |
| 6,989,011 | B2 | | 1/2006 | Paul et al. |
| 7,037,339 | B2 | | 5/2006 | Houfburg |
| 7,153,305 | B2 | | 12/2006 | Johnson et al. |
| 7,207,992 | B2 | * | 4/2007 | Ritland ........................ 606/86 A |
| 7,252,686 | B2 | * | 8/2007 | Carrison et al. ........... 623/17.16 |
| 7,442,210 | B2 | * | 10/2008 | Segal et al. ................. 623/17.12 |
| 2004/0097930 | A1 | | 5/2004 | Justis et al. ..................... 606/61 |
| 2007/0149978 | A1 | * | 6/2007 | Shezifi et al. ................... 606/90 |
| 2008/0039872 | A1 | * | 2/2008 | Catanese et al. .............. 606/139 |

FOREIGN PATENT DOCUMENTS

| | | |
|---|---|---|
| DE | 203 14 708 | 11/2003 |
| DE | 698 18 246 T2 | 7/2004 |
| DE | 103 44 019 B3 | 5/2005 |
| WO | WO-00/44319 A1 | 8/2000 |
| WO | WO-00/74605 A1 | 12/2000 |
| WO | WO-2004/019829 A1 | 3/2004 |

OTHER PUBLICATIONS

International Search Report from PCT/US06/06638, mailed Feb. 5, 2007 (2 pages).

Written Opinion of the International Searching Authority from PCT/US06/06638, mailed Feb. 5, 2007 (3 pages).

* cited by examiner

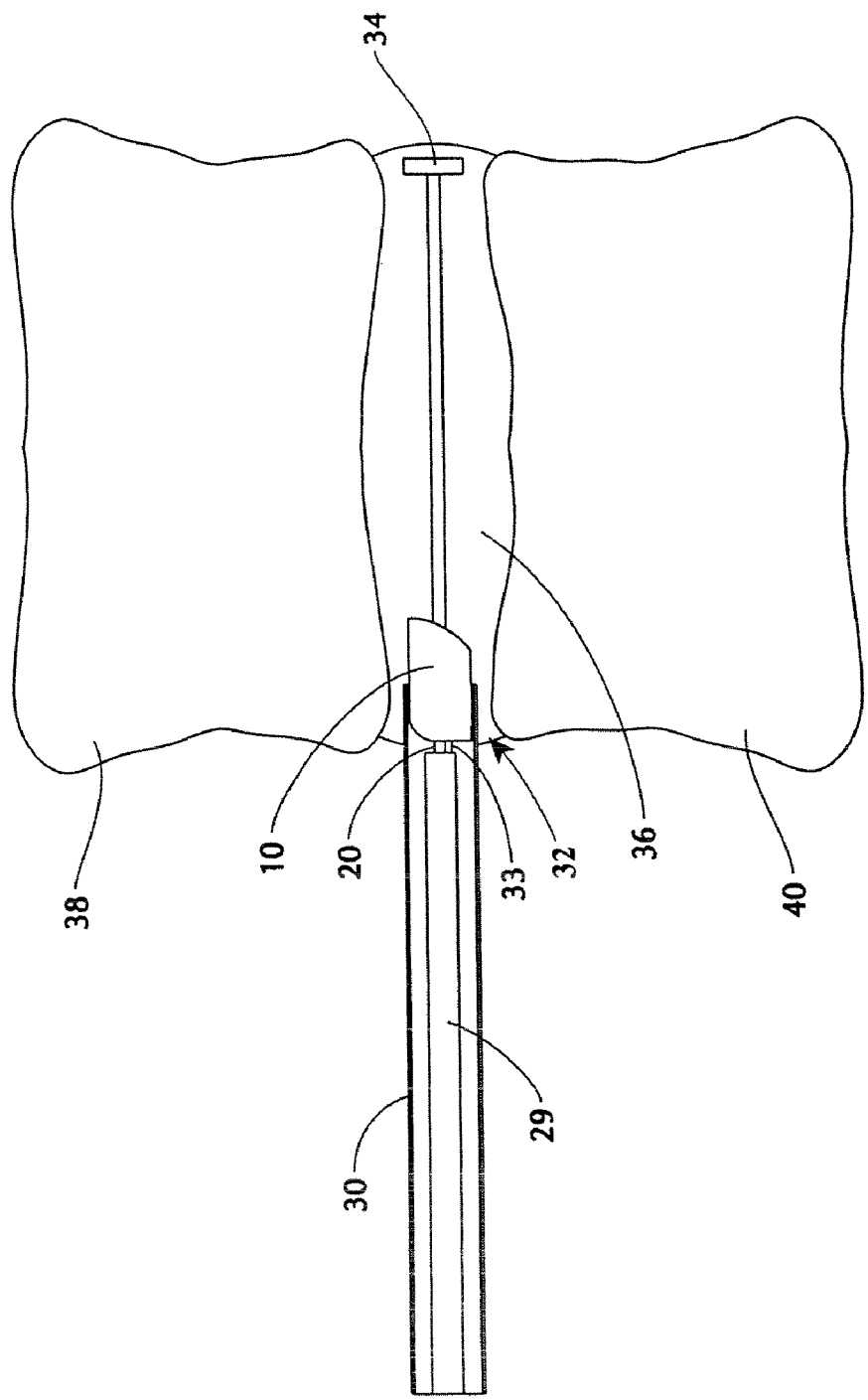

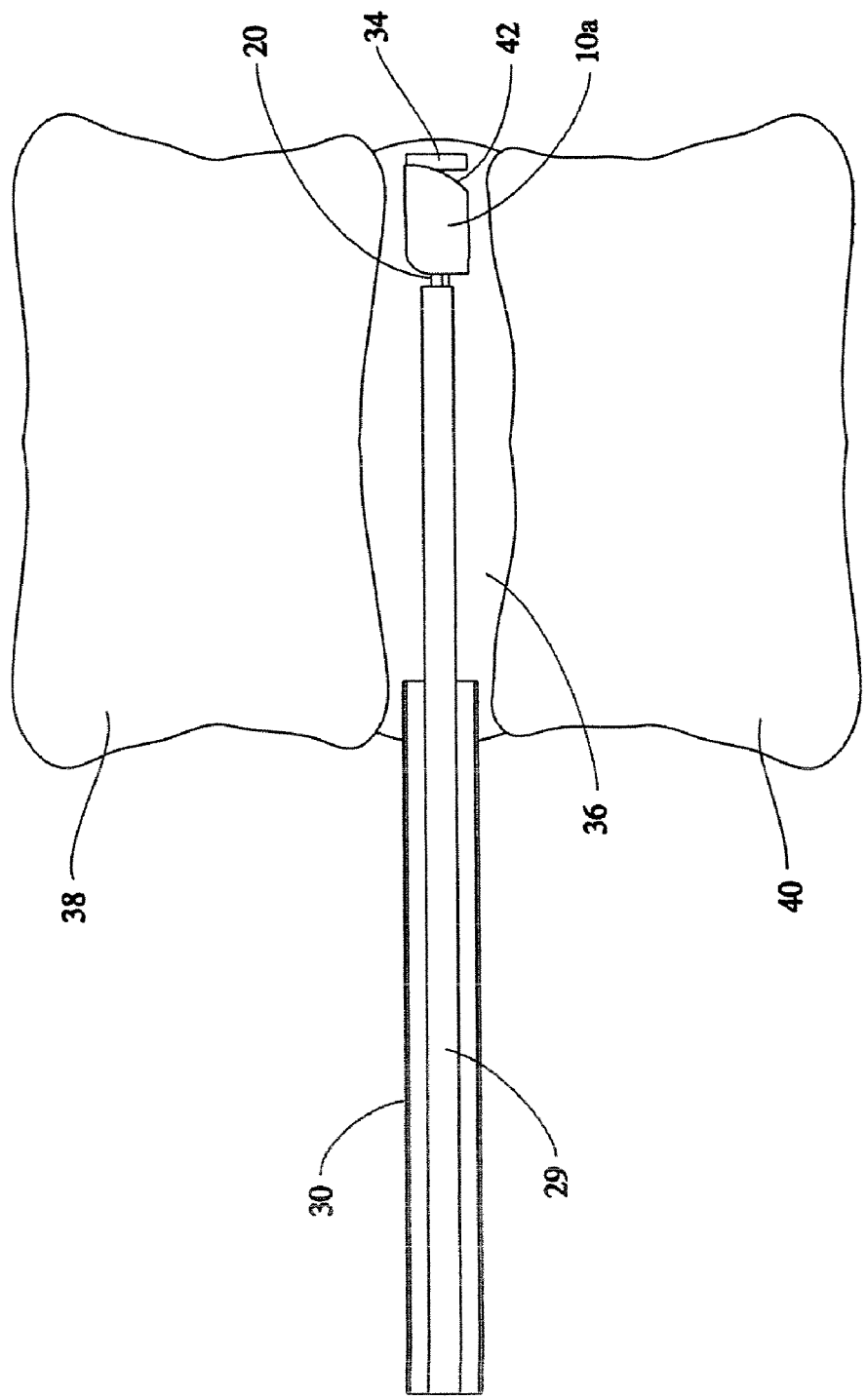

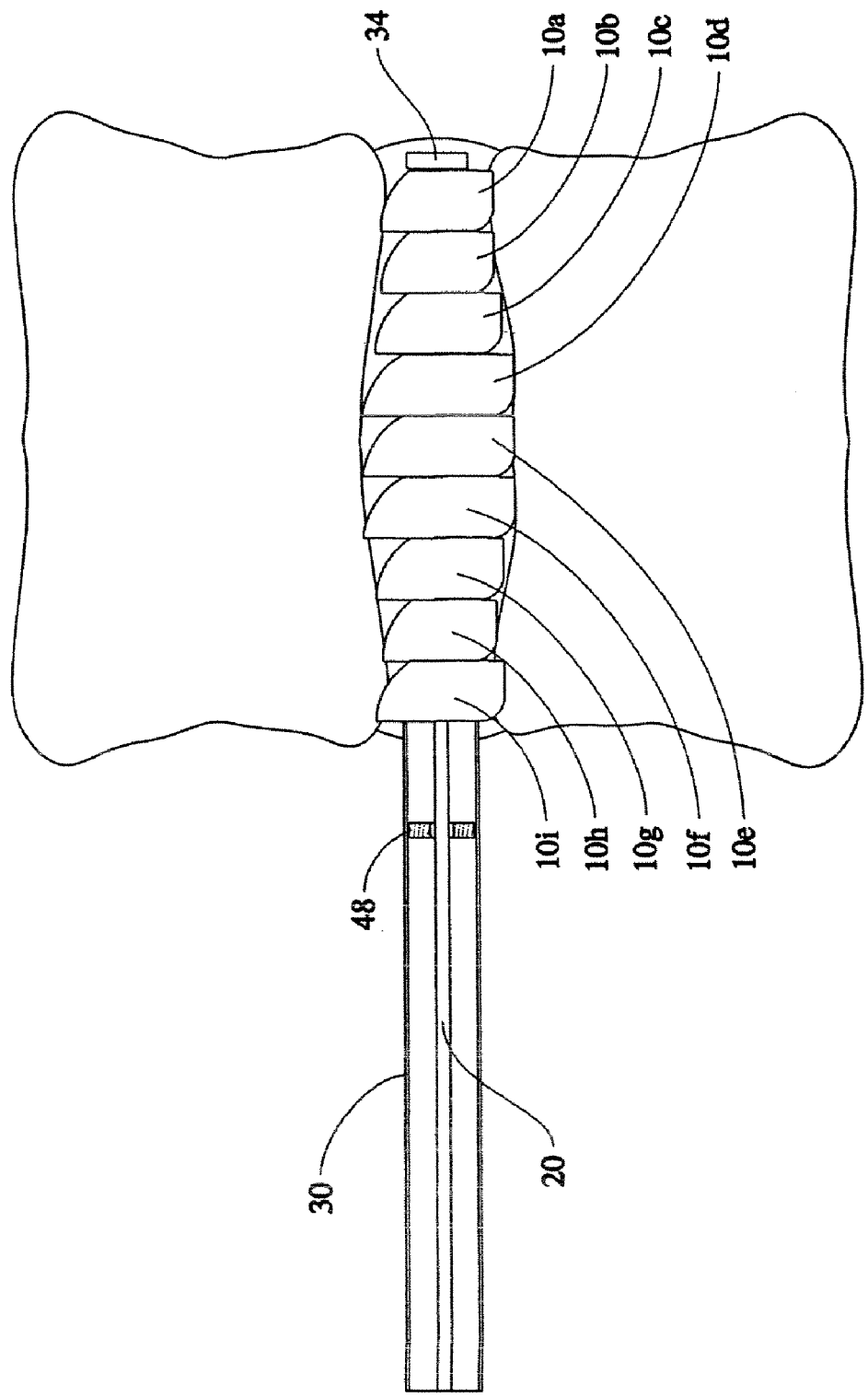

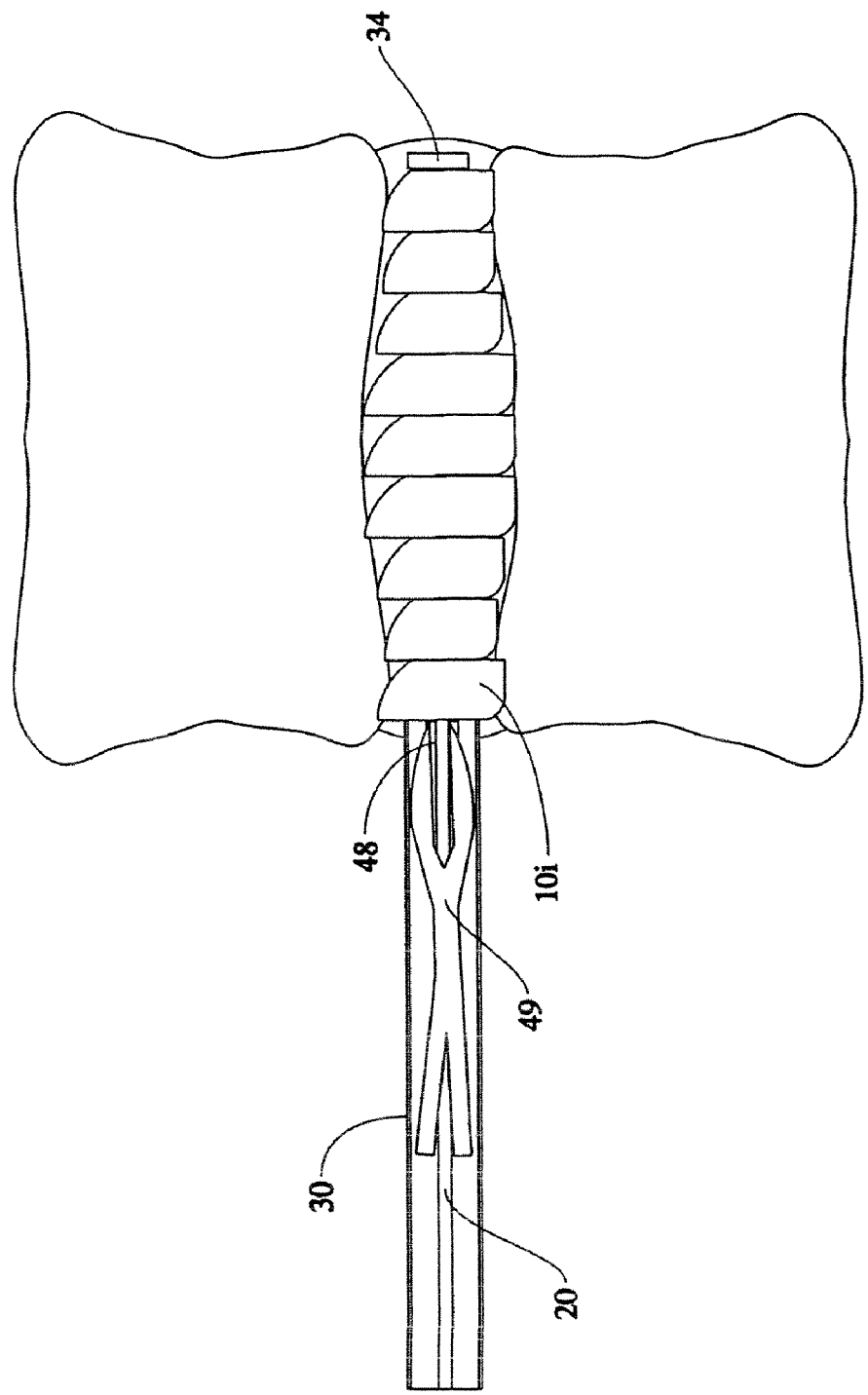

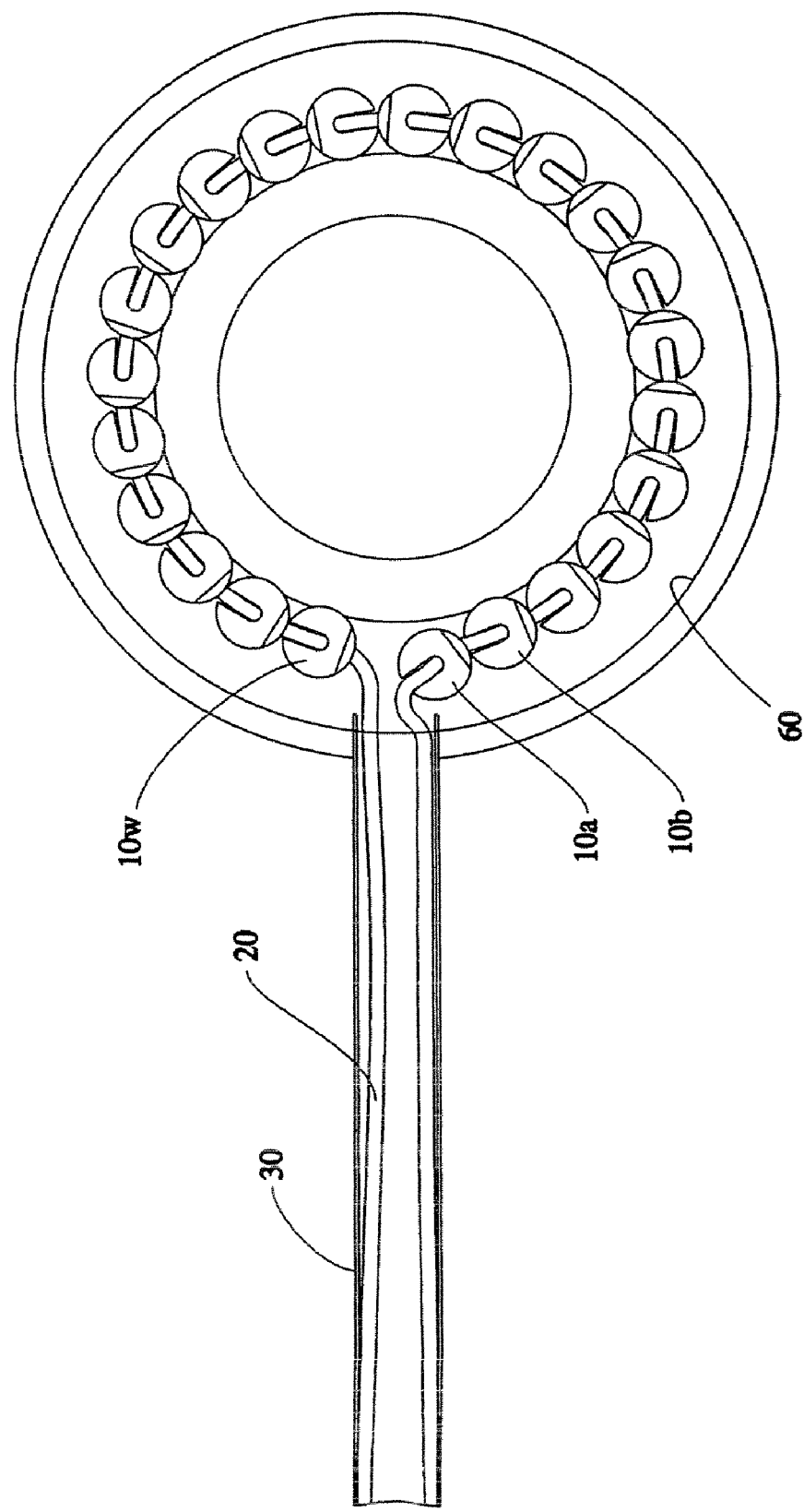

LINKED SLIDEABLE AND INTERLOCKABLE ROTATABLE COMPONENTS

REFERENCE TO RELATED APPLICATIONS

This disclosure is entitled to the benefit of the filing date of U.S. Provisional Application No. 60/656,029, filed Feb. 24, 2005, as to all subject matter commonly disclosed therein.

FIELD OF THE DISCLOSURE

The device and method described herein include rotatable components or segments, delivered in a first orientation relative to a component guide, e.g. horizontally, into a tissue space such as the interbody vertebral space that, after delivery, rotate to a second, different orientation relative to the component guide, such as into a permanent vertical standing position. This allows for maximum distraction of the cavity space such as adjacent vertebra end plates, while using a minimal invasive surgical (MIS) approach. The device is able to be tightened with the method described below providing long-term stability. The device can be used as a distraction instrument and/or permanent implant that can be used for interbody fusion, nuclear replacement, or anywhere in the body where a stable distraction of tissue and/or the implantation of material such as a device with an MIS approach is desired.

DESCRIPTION OF THE PRIOR ART

Many surgical procedures conducted today require the distraction of tissue and/or the implantation of material such as a device to achieve the medical objective of the surgeon. Traditional techniques utilize bulky instruments that necessitate large openings for entry and access into the area of treatment resulting in additional trauma, longer healing times, and higher risks of complications. The trend is growing for the use of minimal invasive surgical techniques for the treatment of various conditions including implantation of various devices in the body. However, current distraction instrumentation limits the use of MIS techniques.

A similar problem exists with the delivery of existing implants themselves. For example, in the area of treatment for degenerative disc disease there are several applications where the implantation of a device through MIS surgical techniques is strongly desired, but not feasible due to the entry portal size being determined by the size of the implant. Thus, for example, current implantations of artificial discs, nucleus replacement, or interbody fusion devices require the removal of a large portion of the annulus, resulting in an increased likelihood of movement or displacement of the device from the desired location within the interbody space.

One application for the disclosed device is as a distraction instrument and/or implant for Interbody Spinal Fusion, which is the method of choice today for the treatment of degenerate disc disease or any other serious spinal instability caused by trauma or other deformities. The object is to correct the loss of disc space and eliminate the motion between the vertebras. Spinal fusion is accomplished through several methods. One technique could be to remove a portion of interbody disc tissue from the interbody space and insert materials such as bone graft that results in the fusion of the two adjacent vertebras. Other conventional methods include the use of pedicle screws, rods, hooks and/or plates on their own, or more typically, in concert with the insertion of such interbody materials. These devices are attached to the adjacent vertebra external walls or pedicle paths to control the vertebral movement around the affected area.

More recently, less invasive techniques for fusion have been utilized, such as interbody fusion implants rather than external devices. Examples include a variety of spinal fusion cages, use of allograft implants and others. These methods, however, show high failure rates due to the inability to stabilize the site sufficient for successful fusion to occur. Like other interbody spinal treatment techniques, current interbody fusion techniques require large openings through the annulus wall into the spinal region.

Newer interbody techniques address some of the issues created by traditional methods. In Stone, U.S. Pat. No. 6,387,130, a plurality of implants are inserted into the intervertebral area by sliding them over an elongated member and abutting them to each other forming two "C" shapes on each side of the interbody area. One advantage this method provides is the use of minimally invasive surgical (MIS) techniques, thereby reducing the size of the opening and reducing collateral damage to the surrounding tissues. It also provides a more dimensionally compatible implant to provide more efficient load transfer support between the adjacent vertebra end plates. The Stone implant has limited capabilities for distraction within the interbody space and the size of the opening in the annulus wall must coincide with the vertical height of the implant.

In Johnson, U.S. Pat. No. 6,595,998, the implant device allows distraction to occur by inserting a plurality of wafer-shaped implants that can slide under one another thereby allowing stacking between the adjoining vertebra, allegedly causing restoration of the intervertebral height that existed prior to the disc compression or collapse.

The Johnson wafer-shaped implants have multiple layers of vertically stacked implant segments. While they are connected and have interlocking features, any vertically stacked composite of components has a greater potential for instability within the interbody space. Since it is necessary to minimize movement between vertebras with interbody fusion techniques, any instability due to such vertical stacking is unacceptable for effective use in an intervertebral space.

SUMMARY OF THE DISCLOSURE

Described herein is a tissue distraction and/or implant system including one or more components which can be delivered with minimal invasive surgical techniques. After delivery into the intervertebral space, the components of the present disclosure rotate might horizontally stack when forced together to create a larger composite. The rotatable components are designed to allow delivery through at least one relatively small diameter delivery cannula into the intervertebral space. The delivery cannula passes through an access portal or percutaneously to gain access to the intervertebral space. One or more rotatable components slide over a component guide that passes through each of the components. The component guide could be one, two, or more members, (e.g. rods, wires, lines, or suture) and could be made with rigid or flexible materials. While it is preferable for the component guide to pass through or close to the center of each of the rotatable components, there may be applications for which the component guide passes though the rotatable components at a location other than their centers. There also might be two or more component guides for each component.

The component guide preferably has a so-called "deadman" at a distal end of the component guide, which serves as a stop member. The components are designed so that they can slide along the component guide in a first orientation, such as in what is referred to herein as a horizontal orientation, into the intervertebral space, through the delivery cannula. A driving probe is inserted into the delivery cannula and a portion of the driving probe is received in a small relief immediately adjacent, and open to, a trailing or proximal end of the implant component. The driving probe allows for precise directional and rotational control of the rotatable component as it is delivered, in the first orientation, along the component guide, and rotated to a second, different orientation relative to the component guide, which may be substantially perpendicular to the first orientation.

As the first rotatable component reaches the distal end of the component guide and makes contact with the dead-man, the first component rotates to the second orientation, that is, an orientation different from, such as substantially perpendicular to, the orientation of the rotatable component as it was advanced along the component guide toward the distal end of the component guide. In its new orientation, the first rotatable component may be positioned to distract the adjacent tissue, such as the vertebra end plates because the component's long axis geometry is dimensionally larger than the component's perpendicular dimension. The rotation of the first component as it makes contact with the dead-man is facilitated by a curved geometry on the distal end of the rotatable component. Subsequent delivered components, if any, rotate as they make contact with the preceding rotatable component and interlock with each other. The rotation of the subsequent components is facilitated by a combination of curved geometry of the proximal and distal ends of the rotatable component.

By repeating this insertion process with components of various precise vertical height dimensions chosen to distract the desired tissue, such as the vertebra end plates, the curvature of a tissue space such as the interbody space between the vertebra end plates may be mimicked by the horizontal stacking of the rotatable components, each component of a specific distraction height being rotated to a second, e.g. vertical, orientation. In some variations of delivery all the components might be delivered horizontally, and after all the components are in the desired space, then all components are rotated simultaneously. This would provide better load distribution within the distracted area, as compared to individual rotation of the respective components. The components might also be delivered and rotated in sets of two, three, or more, depending on the desired result. In some variations of delivery, the components might be delivered in two or more rows, with the rotation of components in each respective row being in a direction opposite to that of adjacent row(s) of components.

When the desired distraction height within the tissue cavity such as with vertebral end plate coverage is achieved within the space with the rotatable components, and a permanent implant is desired, the components may then be tensioned together by tying the component guide off at the proximal end of the last component, or securing the tightened implant with a locking device, and cutting the remaining guide to minimal length. The locking device may include a locking washer, threaded devices, bonded devices, or unidirectional sliding devices. In some variations described herein, the tensioning of the component guide, rather than a driving probe, may be used to rotate the plurality of rotatable components from the first orientation to the second orientation. In other variations the rotatable components might have a separate tensioning member passing through the components that imparts rotation to the components when tensioned, while the component guide remains static. The delivery cannula is removed and the opening portal is then closed.

The rotatable components could be designed so that each component has a pair of slotted openings, preferably in the form of a first elongate, centrally disposed slot extending between the distal end of the rotatable component and approximately a mid-point of the component, and a second elongate, centrally connected, symmetrically mirrored (with respect to a diagonal plane bisecting the linkable segment) slot extending between a proximal end of the rotatable component and approximately the mid-point of the component. The two slots overlap one another at each of two bores running the length and height of the rotatable component. The second elongate slot extends in an opposite direction from the first elongate slot. This pair of slotted openings allows the component guide to remain tethered within the body of the rotatable component. This slot configuration allows the rotation of the rotatable component with the component guide therein, without undesired movement of the component guide. Where the components have more than one component guide ember, at least a pair of slotted openings would be provided for each guide member. As a result, the rotatable components may achieve greater distraction of the space than existing methods can provide through minimal invasive surgical techniques.

A rotatable component of this disclosure can also include a male member on its side that allows the component to interlock into a female opening in an adjacent component. The components might also have depressed tracks along the sides on the top of the components with a corresponding rail on the bottom of the adjacent component that allows for further interlocking and stability of the device upon rotation of respective components to their second orientation relative to the component guide.

One benefit of utilizing the rotatable components of the present disclosure as an implant is that separate distraction instruments are not required to pre-distract adjacent tissue such as vertebras surrounding an interbody space. One or more rotatable components are delivered in a first, e.g. horizontal, orientation, and only rotated to a vertical (or other) orientation upon delivery to a location at which no pre-distraction for the placement of the components as an implant is necessary since the rotatable components would accomplish any necessary distraction themselves as a result of the rotation. In addition, the device could be used as a distraction instrument itself, and removed after the desired treatment is completed. For example, the placement of a hydrogel nucleus replacement device could be delivered through smaller MIS access procedures by utilizing the disclosed device as a distraction instrument. The device could also be useful where a smaller size portal entry through tissue such as the annulus is desired but limited due to the vertical height of the implant itself. By delivering one or more of the components horizontally and then rotating and assembling the implant within the interbody space the smaller portal entry can be achieved while maintaining the full desired vertical height of the construct. This aspect of the present disclosure would be advantageous anywhere that a minimal entry portal is desired even where no distraction of tissue is needed and the height of the desired implant is equal to or less than the height of the tissue space that the device is being implanted in, such as the interbody space between the vertebra.

Another advantage is that the components can be delivered in a manner that allows them to precisely follow the curvature of the inside of the annulus wall. Alternative designs of the components would facilitate the ability of the device to form a precise arc. They also can have various vertical heights to allow the precise desired distraction of the inter-body space without changing the portal opening size. Also, unlike other methods such as disclosed in Johnson, the rotatable components described stack horizontally rather than vertically. This horizontal stacking provides optimal transfer of load through each component itself rather than a composite of components like in Johnson, thereby substantially reducing the potential for slippage or other instability of the delivered device. In some applications each rotatable component might support its own load bearing eliminating the need for stacking altogether. Some applications may only require one rotatable component to accomplish the desired medical result of distraction and/or implantation of a permanent device whether it is the disclosed device or another device. Rotatable components can be delivered in straight lines, curved lines, or in a 360° circle within or around the inside of the annulus wall.

The shape of the rotatable components can vary and can, by way of example, have a cross-sectional shape (where the cross-section is taken through a plane perpendicular to the longitudinal axis of the implant component) which is rectangular, oval, oblong, hexagonal, octagonal, or other multifaceted shape. Also disclosed are alternative designs that include hinged components and ring designs which might further enhance the performance of the device. The rotatable components can also include a relief or cavity adjacent the two vertical ends to provide additional pressure (for fusion use) or flexibility (for nuclear replacement). This relief or cavity could also increase the load bearing surface area of the component resulting in a wider disbursement of load through the component.

The height of the rotatable components can vary to meet the variances in desired distance between tissue such as the vertebra end plates. While the rotatable components may have any height, for interbody fusion it is preferable for rotatable components of the present disclosure to have a height in orange from about 5 mm to about 21 mm, and even more preferable for the rotatable components to have a height in a range from about 5 mm to about 17 mm.

Materials for the implant segments can be hard so as to, for example, provide crush strength or other strength, or alternatively, be flexible, for example to provide controlled motion desired in nuclear replacement procedures. The rotatable segments may comprise, consist of, or consist essentially of any medical grade material including by way of example the following materials:

Bioabsorbable (or bioerodible) and non-bioabsorbable (or non-bioerodible) material; metals, including, but not limited to, biocompatible metals and alloys, such as stainless steels, gold, silver, tantalum, cobalt, chromium, titanium, platinum, rhodium, rhenium, ruthenium, and other alloys thereof, combinations thereof, or other equivalent materials; ceramic materials, including, but not limited to, alumina, carbon or tricalcium phosphate or sintered masses or single crystals of hydroxyapatite; refractory metal and semi-metal oxides (tantalum oxides, aluminum oxides), phosphates (calcium phosphates), phosphides, borides (niobium borides, tungsten borides), carbides (aluminum carbides, boron carbides, niobium carbides, silicon carbides, tantalum carbides, titanium carbides, tungsten carbides, vanadium carbides, zirconium carbides), nitrides (boron nitrides, chromium nitrides, silicon nitrides, tanalum nitrides, titanium nitrides, zirconium nitrides), silicides (tantalum silicides, tungsten silicides, zirconium silicides), their mixtures, variously sintered as porous particulates or as solid formations; inorganic materials, including, but not limited to, hardened glasses including oxides of silicon, sodium, calcium and phosphorous and combinations thereof; polymers, including, but not limited to, elastomers (natural and synthetic rubbers, silicone rubbers), polymethyl methacrylate (PMMA), polyetheretherketone (PEEK), polymethymethacrylate (PMMA), polyglycolic acid and/or polylactic acid compounds, polyvinylchloride (PVC), polyethylene (PE, HDPE, UHMWPE, etc.), polystyrene (PS), polyesters (PET, polycaprolacton, polyglycolied, poylactide, poly-p-dixanone, poly-hydroxy-butylate), polyamides (Nylons, aromatic polyamides), polypropylene (PP), fluorocarbon polymers (PTFE, PTFCE, PVF, FEP) and other biocompatible materials, collagen and/or collagen derivative preparations alone or in combination with other biomaterials, chitin and chitosan preparations; bone derived materials, including, but not limited to, bone autografts, bone allografts, bone xenografts, bone-derived tissue, bone-derived collagen, and the like. Any combinations of these materials may be used as a segment material. Rotatable components may include pellets of any of these materials, or combinations thereof. Finally, suitable known materials acceptable for use as rotatable component materials include various osteogenic and osteoinductive compositions, and combinations thereof. Certain glassy carbon forms are also quite useful.

Rotatable component materials may also comprise radiopaque materials to enhance visualization of the implant, or the rotatable components may each incorporate a radiopaque material as apart thereof (e.g., coatings, dispersed, or core materials). Examples of radiopaque materials include but are not limited to, barium sulfate, tungsten, bismuth compounds, tantalum, zirconium, platinum, gold, silver, stainless steel, titanium, alloys thereof, combinations thereof, or other equivalent materials for use as radiographic agents.

The component guide can be stiff or flexible with a simple or complex cross-section depending on the desired physician objective. The component guide can comprise a string or fiber or wire, variously of single or multiple strands. Suitable examples of fibers include those used as suture materials, biodegradable or not, e.g., polylactic acids, polyglycolic acids, mixtures and copolymers of polylactic and polyglycolic acids (PGLA such as "Vicryl" from Ethicon and "Dexon" (from Davis & Geck), polydioxanone, various Nylons, polypropylene, silk, etc.). The wires may comprise one or more filaments comprising suitably biocompatible metals or alloys, e.g., stainless steels, titanium, or super elastic alloys.

An additional advantage is the various embodiments disclosed herein eliminate potential stress risers that can result from layered or other improper load distribution.

The rotatable component system of the present disclosure can be utilized in any area where distraction of tissue and/or the implantation of implants through minimal invasive surgical techniques are desired. The preferred method is for the treatment for degenerative disc disease such as for interbody fusion or other interbody implants such as nuclear replacement.

BRIEF DESCRIPTION OF THE SEVERAL VIEWS OF THE DRAWING

FIG. 1b is an enlarged perspective view of the rotatable component of FIG. 1a;

FIG. 3b is a leading or distal end view of the rotating component of FIGS. 1a-1c and 3a, taken in the direction of lines 3b-3b of FIG. 3a;

FIG. 4b is a side plan view of the rotatable component system of FIG. 4a, additionally showing a driving probe and a first rotatable component, of the type shown in FIG. 1, beginning to exit the delivery cannula;

FIG. 4c is a side plan view of the rotatable component system of FIGS. 4a and b, showing the first implant component making initial contact with the dead-man at the distal end of the intervertebral area;

FIG. 4i is a side plan view of the rotatable component system of FIGS. 4a-h showing a plurality of rotatable components substantially filling the cavity, and showing a locking device (shown in cross-section) being delivered through the delivery cannula along the component guide;

FIG. 4k is a side plan view of the rotatable component system of FIGS. 4a-j, and a crimping tool used to secure the locking device in its final position;

FIG. 15 is a side plan view of an implantation utilizing an rotatable component system of the present disclosure, wherein rotatable components are delivered, rotated, and stacked in a 360° circle around the inside of an annulus wall and encapsulating a biologic device;

DETAILED DESCRIPTION OF THE PREFERRED EMBODIMENTS

Figure 1A:
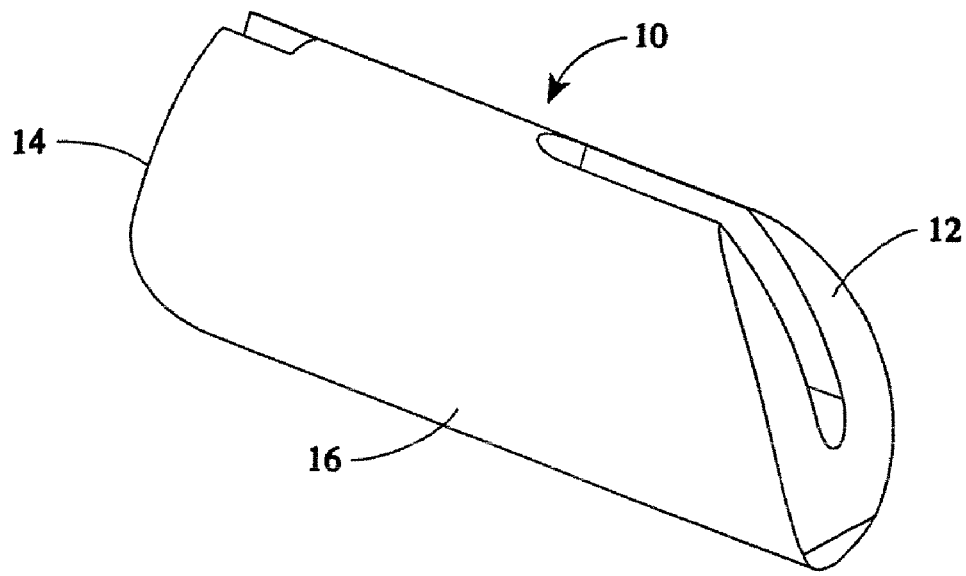
FIG. 1a is an enlarged perspective view of a first embodiment of a rotatable component of the present disclosure.

An implant system of the present disclosure includes a plurality of rotatable segments 10 of a first embodiment, as shown in FIGS. 1a-b, 4b-k, and 10. Each rotatable segment 10 has a leading or distal end 12, a trailing or proximal end 14, and a main body 16. A first hollow bore 18 extends the length of the rotatable segment 10, i.e. the hollow bore 18 extends from the leading or distal end 12, through to the trailing or proximal end 14.

The first hollow bore 18 is sized to accommodate a component guide 20 such that the rotatable segment 10 may be advanced along the component guide 20. For reasons explained below, the rotatable segment 10 also includes a first slotted opening 22 and a second slotted opening 24. The first and second slotted openings 22, 24 are contiguous with the hollow bore 18. The first slotted opening 22 extends between the distal end 12 and a second hollow bore 26. The second hollow bore 26 extends the horizontal height (i.e., the height when in the horizontal orientation, described below) of the rotatable component 10, i.e. in a direction perpendicular to the first hollow bore 18.

Figure 16A:
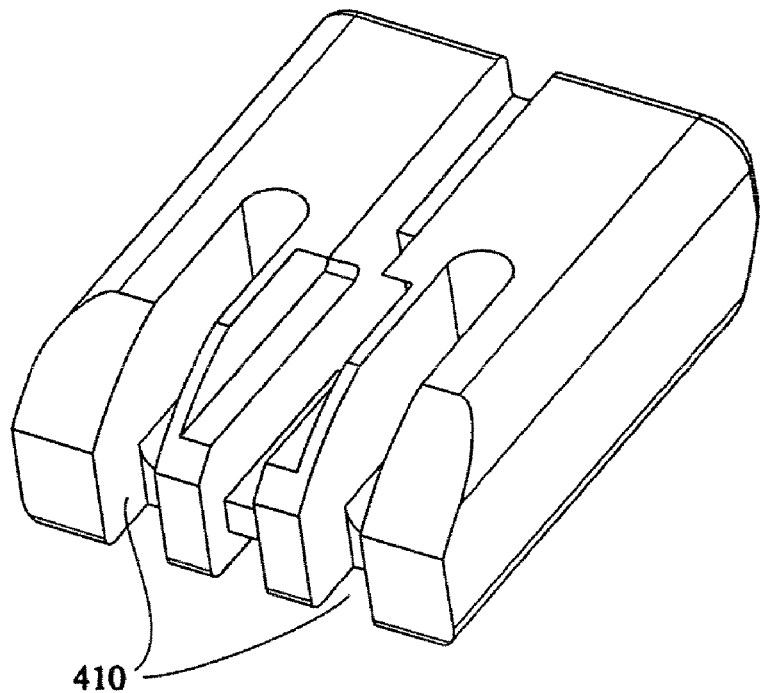
FIGS. 16a and 16b are two perspective views of a rotating component with two hollow bore pathways for the use of two component guides within one component.

In one variation as shown in FIG. 16 a component might have two hollow bore pathways 410 for the use of two component guides within one component.

Figure 1B:
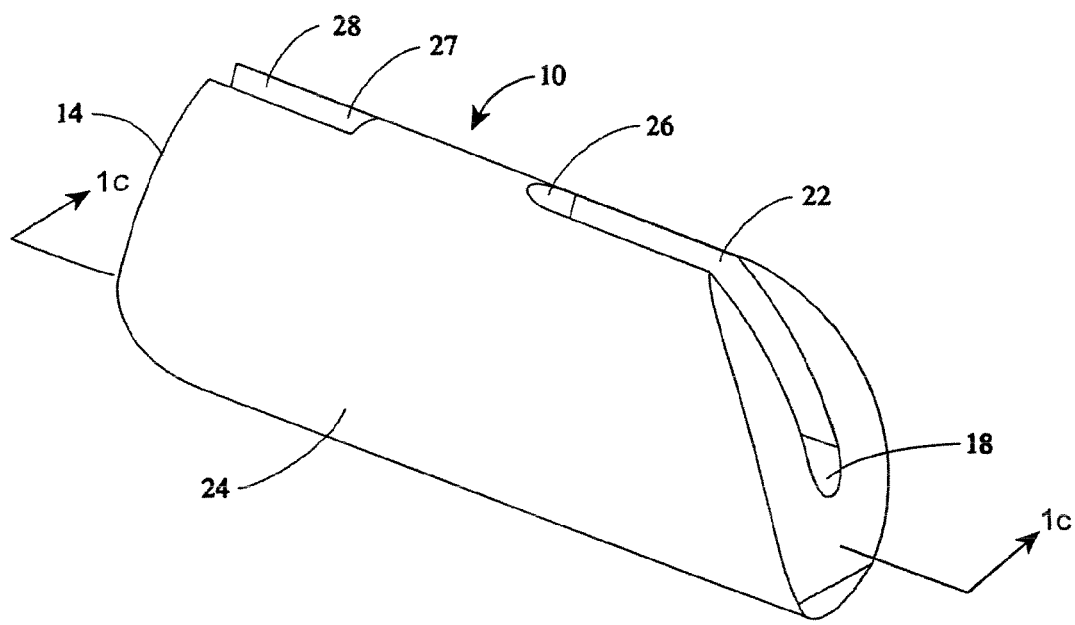
Figure 1C:
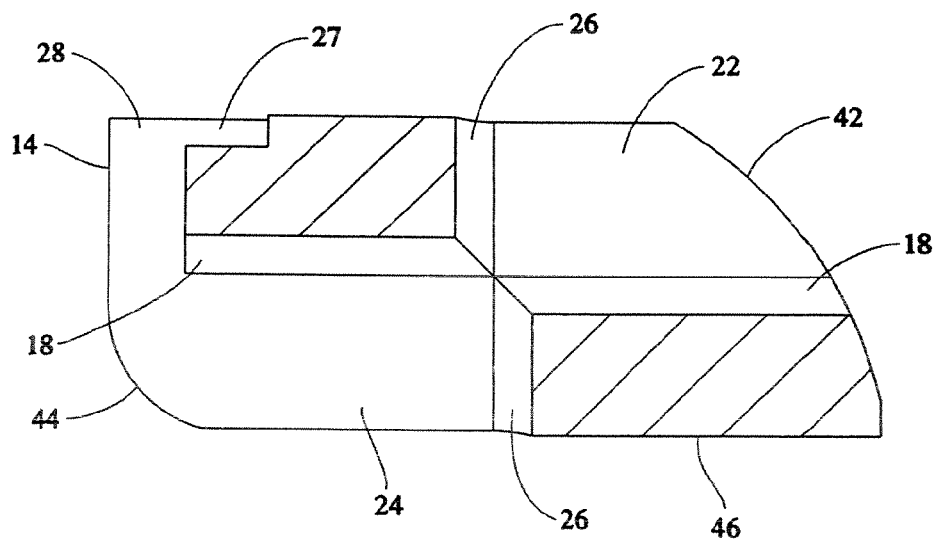
FIG. 1c is a cross-section of the rotatable component of FIGS. 1a and b, taken along lines 1c-1c of FIG. 1b.
Figure 3A:
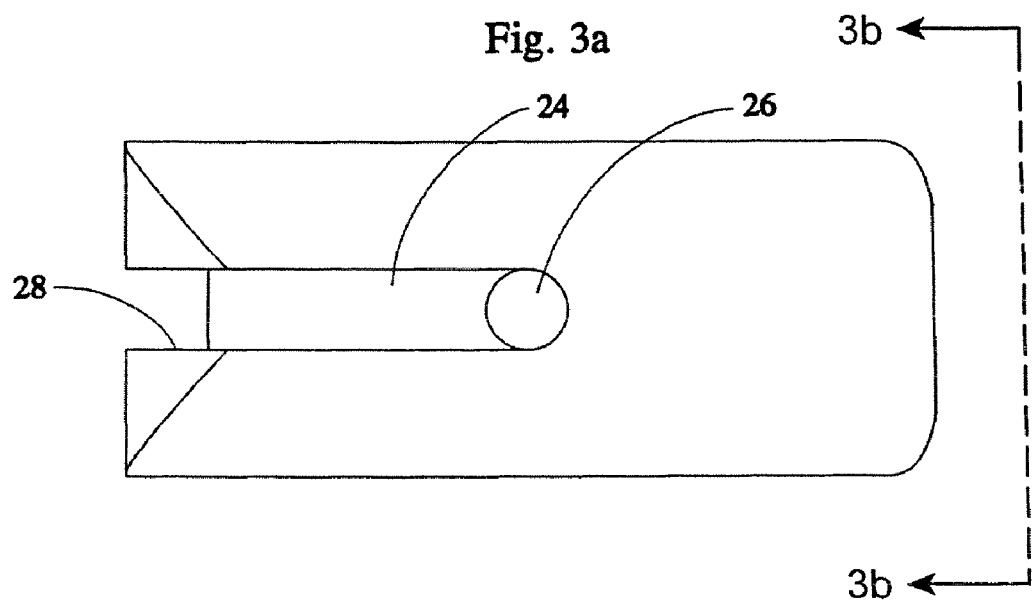
FIG. 3a is a top plan view of the rotatable component shown in FIGS. 1a-1c.
Figure 3B:
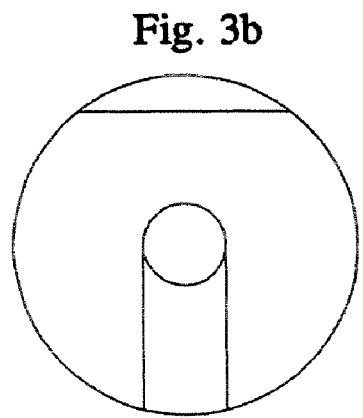
Figure 16B:
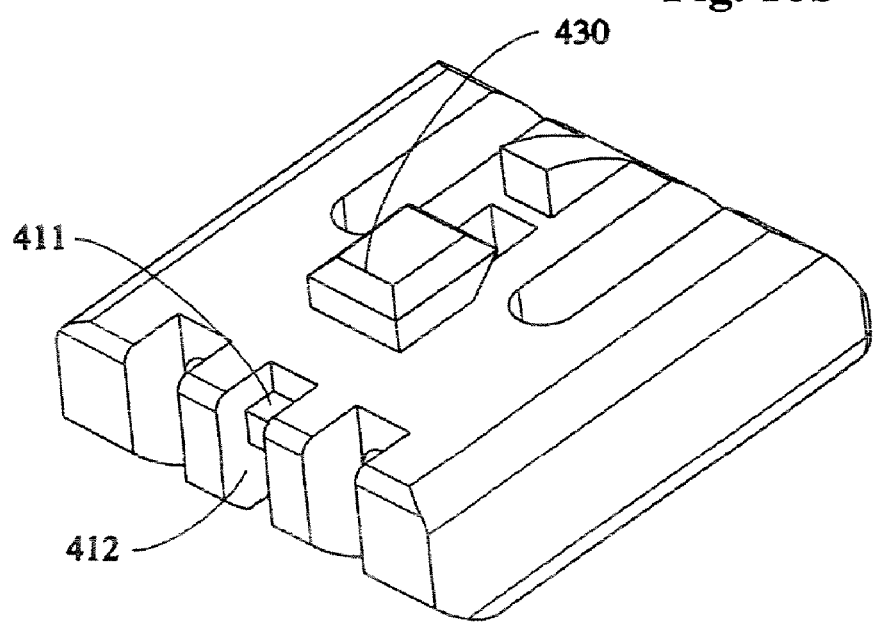

A small relief 28 in the main body 16 of the rotatable component 10 is preferably provided immediately adjacent, and open to, the trailing or proximal end 14 of the implant component 10. This relief 28 advantageously receives a portion of a driving probe 29, which may be used by a physician to exercise precise directional control, including control over advancement, retraction, and rotational orientation, over the rotatable component 10 as the rotatable component 10 is delivered along the component guide 20. The small relief 28 may be contiguous with the second slotted opening 24 and the first bore 18, as shown in FIG. 1c. Additional control could be achieved with the use of a retractable protrusion 37 on the probe 29 that would be inserted into an additional small relief 27 at the distal end of the control relief 28 on the proximal end of the component (see also FIG. 16b, showing relief 411 connected to the probe relief 412) that would prevent premature rotation within the cavity space until retracted.

As best shown in FIGS. 10-13, the driving probe 29 is designed so as to receive, and travel along, the component guide 20. The driving probe 29 has a male projection 33 at a distal end 35 of the probe body 29. It is this male projection 33 that is received in the small relief 28 of the rotatable component 10.

A delivery cannula 30 surrounds the component guide 20 and is inserted through an opening portal 32, thereby isolating the component guide 20 from surrounding tissues. A stop member, or dead-man, 34 is provided at a distal end of the component guide 20 to ensure that the components 10 are retained in a precise location within a tissue space such as the intervertebral space 36 (between two adjacent vertebras 38, 40). This provides for loading and positioning of one or more rotatable components 10 within a tissue space such as an intervertebral space 36 without loading the surrounding non-distracted tissue, while providing the forces required to rotate the components into their desired final orientation.

Figure 4A:
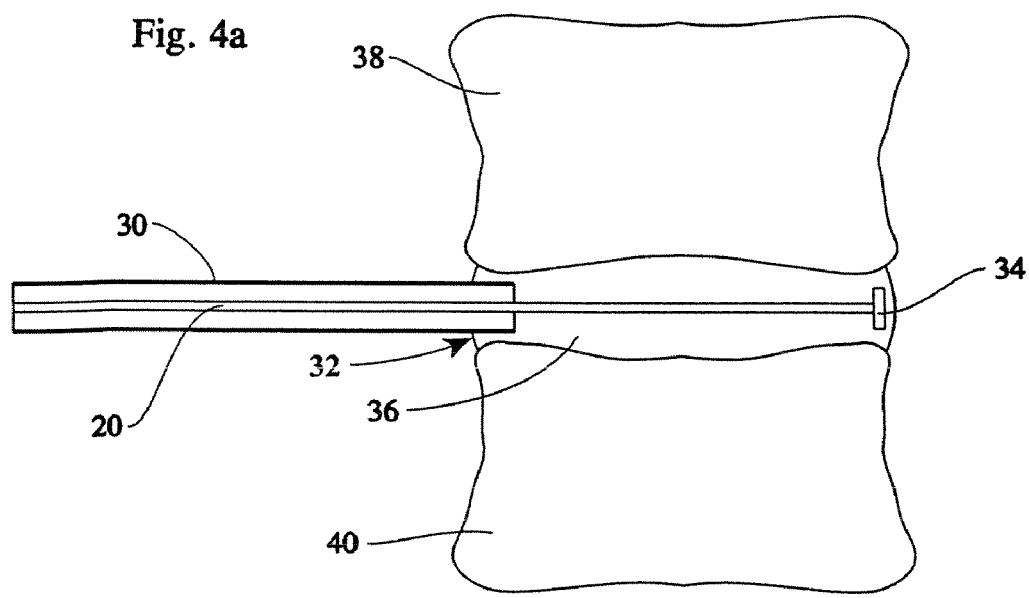
FIG. 4a is a side plan view of a rotatable component system according to the present disclosure, showing a delivery cannula, a component guide, and a stop member or "dead-man" disposed at a distal end of the component guide, with the dead-man deposited within and at a distal end of an intervertebral area.

A first rotatable component 10a is delivered through the cannula 30 such that the component guide 20 is received in, and coaxially aligned with, the first hollow bore 18. The first rotatable component 10a is advanced in this orientation, which for purposes of this disclosure is considered a "horizontal orientation," until the distal end 12 of the first rotatable component 10a makes initial contact with the dead-man 34 at the distal end of the component guide 20, as shown in FIG. 4c. As shown in FIGS. 4d and e, upon making initial contact with the dead-man 34, the first rotatable component 10a rotates to a vertical orientation, i.e. perpendicular to the horizontal orientation of the first rotatable component 10 relative to the component guide 20 as it was delivered through the cannula 30 and approached the dead-man 34. The rotation upon contact with the dead-man 34 is achieved as a result of the loading of the first rotatable component 10a against the dead-man 34 by driving probe 29 or inertia force, and a curved leading surface 42 of the distal end 12 of the first rotatable component 10 (see FIG. 1c). Each rotatable component may also have a curved trailing surface 44 at the proximal end 14 thereof, as shown in FIG. 1c. The curved leading surface 42 of each rotatable component 10 assists the components 10 in initiating rotation upon contact with a dead-man 32 or with the trailing surface of the preceding rotatable component 10.

The first and second slotted openings 22, 24 permit and further facilitate the controlled and precise rotation of each of the rotatable components 10 from a horizontal orientation, in which the first hollow bore 18 is coaxially aligned with the component guide 20, to a vertical orientation, in which the second hollow bore 26 is coaxially aligned with the component guide 20. Without the first and second slotted openings 22, 24, the component guide 20 would undesirably restrict rotation of the components 10.

Figure 22A:
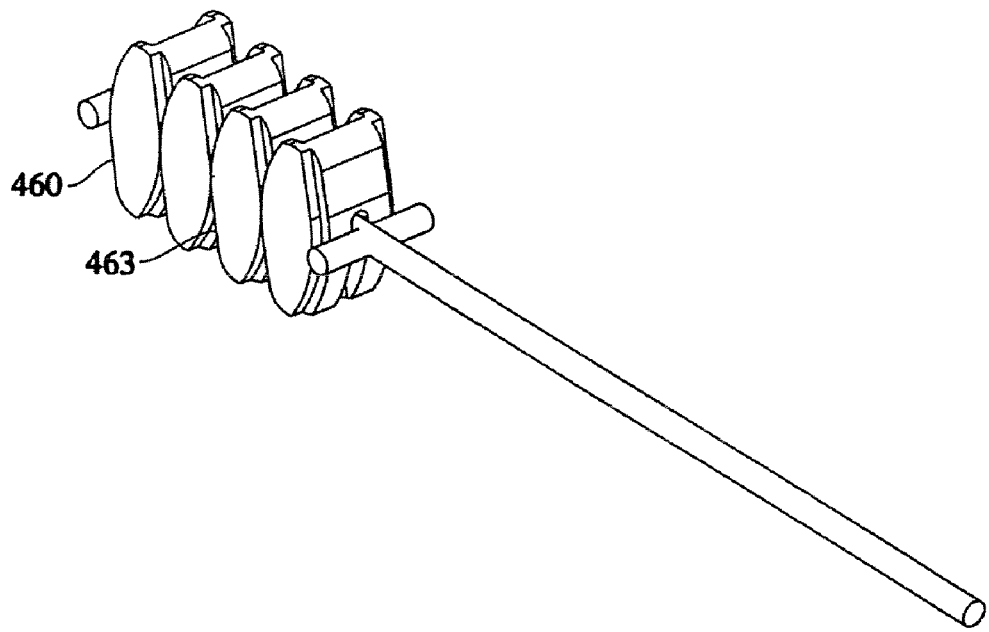
FIGS. 22a and 22b are two perspective views of an alternate connecting design.
Figure 22B:
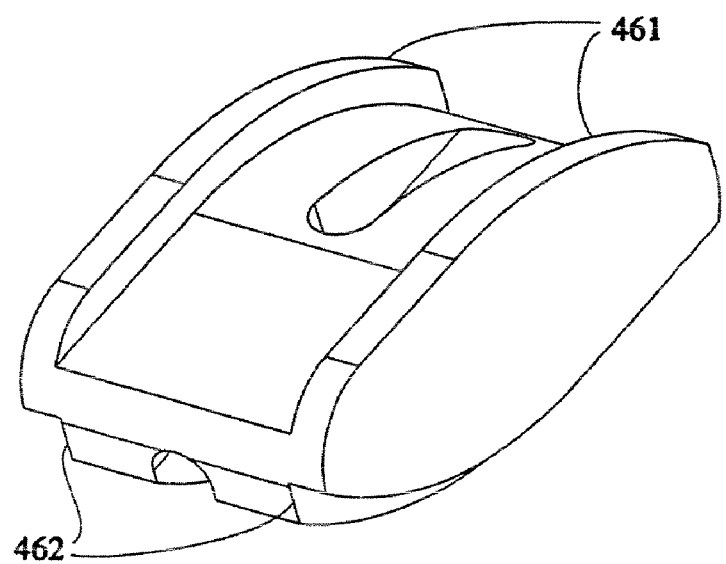
Figure 23B:
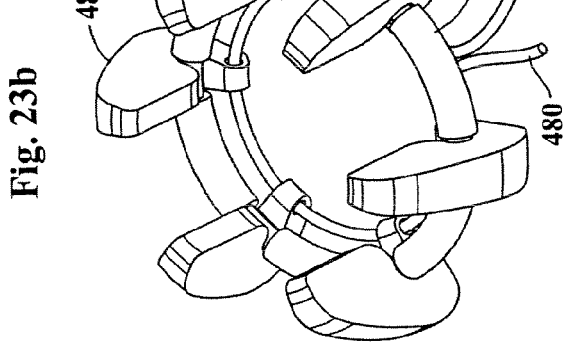
FIGS. 23a-d and 24a-c are various perspective views of further alternative embodiments of the present disclosure, in a ring configuration.
Figure 23D:
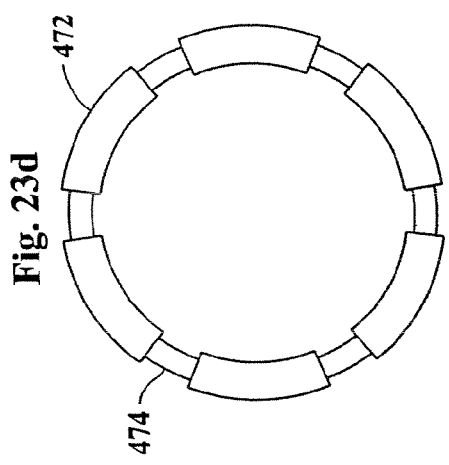
Figure 23A:
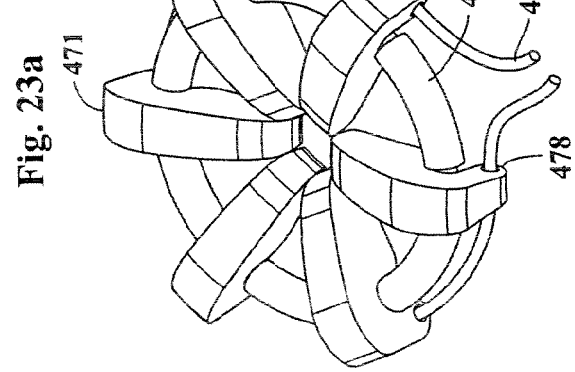
Figure 23C:
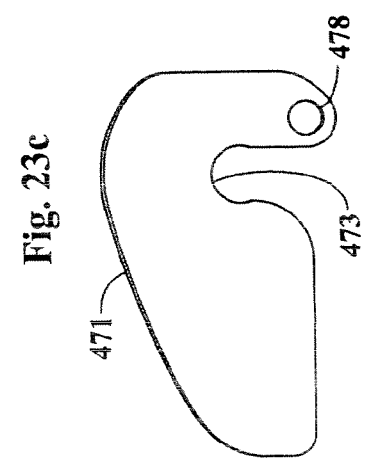

In one variation the component might have an alternative external geometry, as shown in FIG. 22, that assists in maintaining orientation during delivery and after rotation. This version may have elevated tracks or rails 461 on the outer sides of the component 460. The adjacent component may have mating recessed grooves 462 that interlock with the elevated tracks or rails to limit the rotation of adjacent components throughout their travel in the desired first, e.g. horizontal, orientation as well as in the final vertically stacked multi-component assembly 463.

Figure 4G:
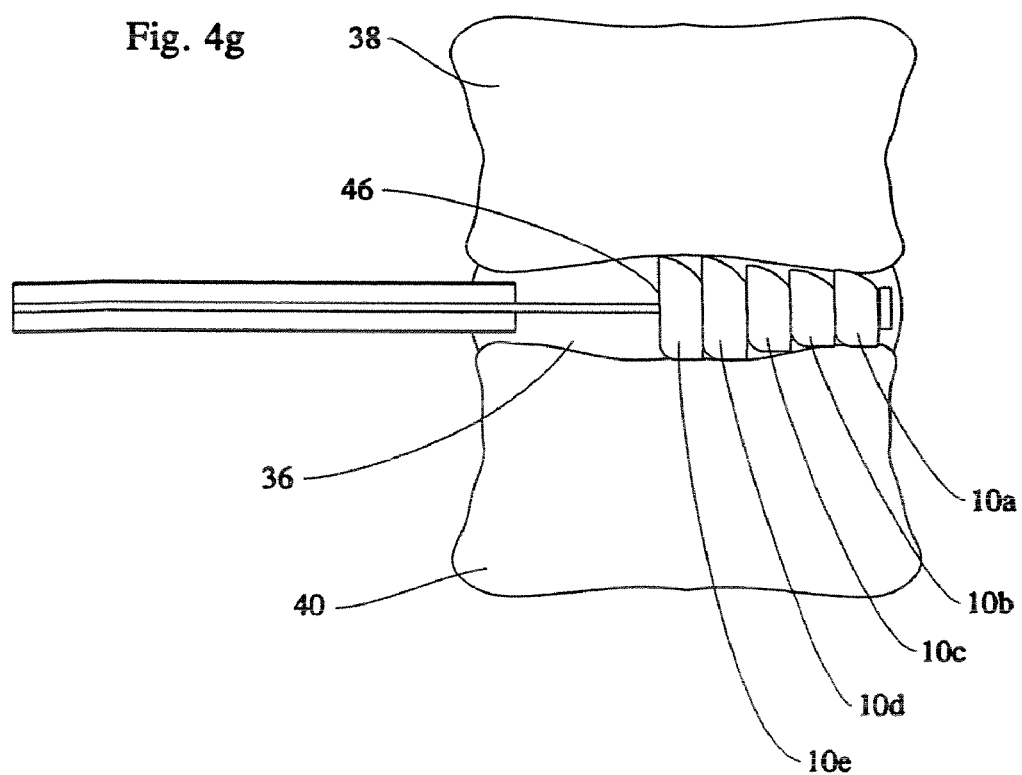
FIG. 4g is a side plan view of the rotatable component system of FIGS. 4a-f, showing that most-proximal of the visible rotatable components also rotated to its final orientation.
Figure 4D:
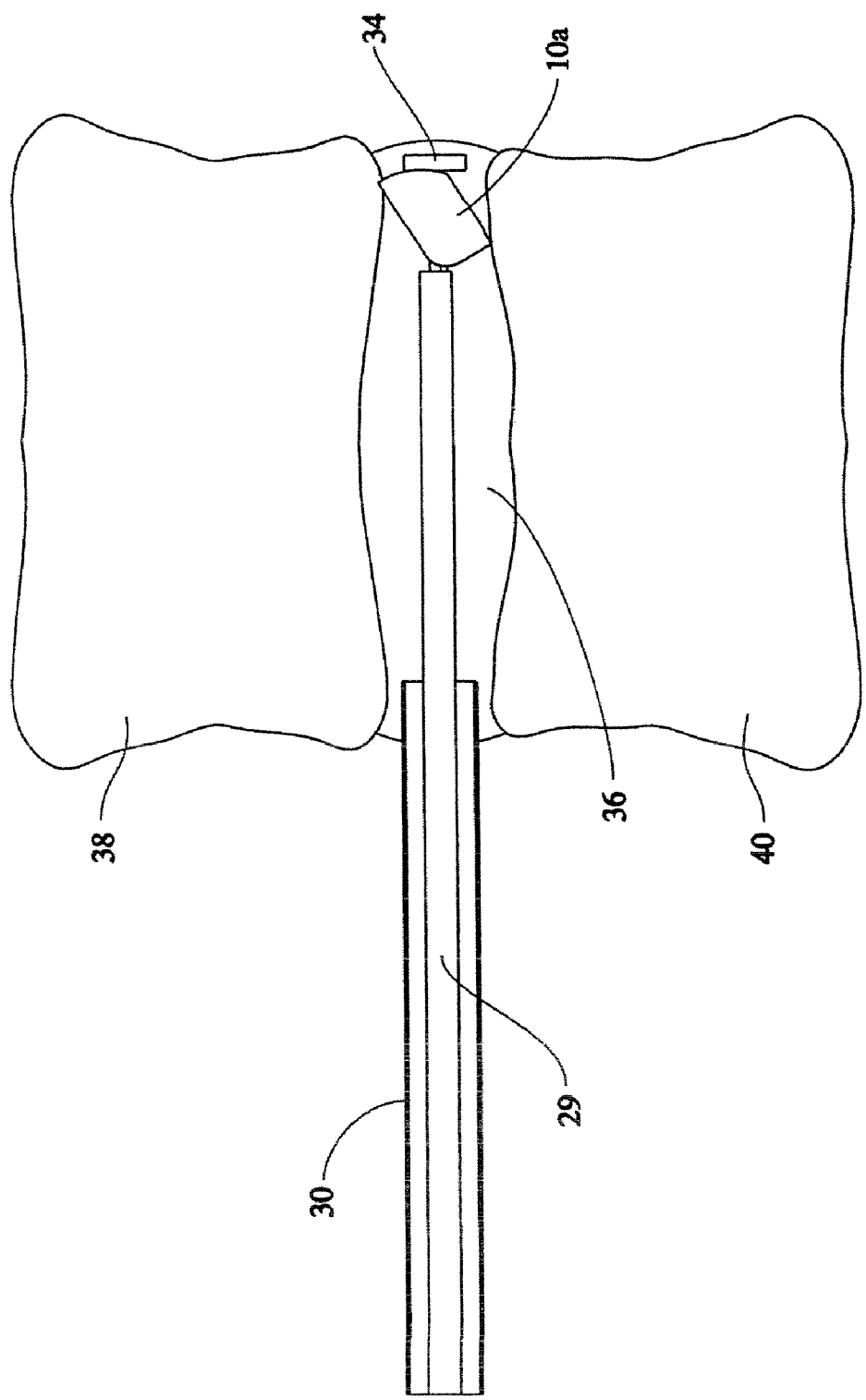
FIG. 4d is aside plan view of the rotatable component system of FIGS. 4a-c, showing the first rotatable component undergoing rotation, after making initial contact with the dead-man at the distal end of the intervertebral area.
Figure 4E:
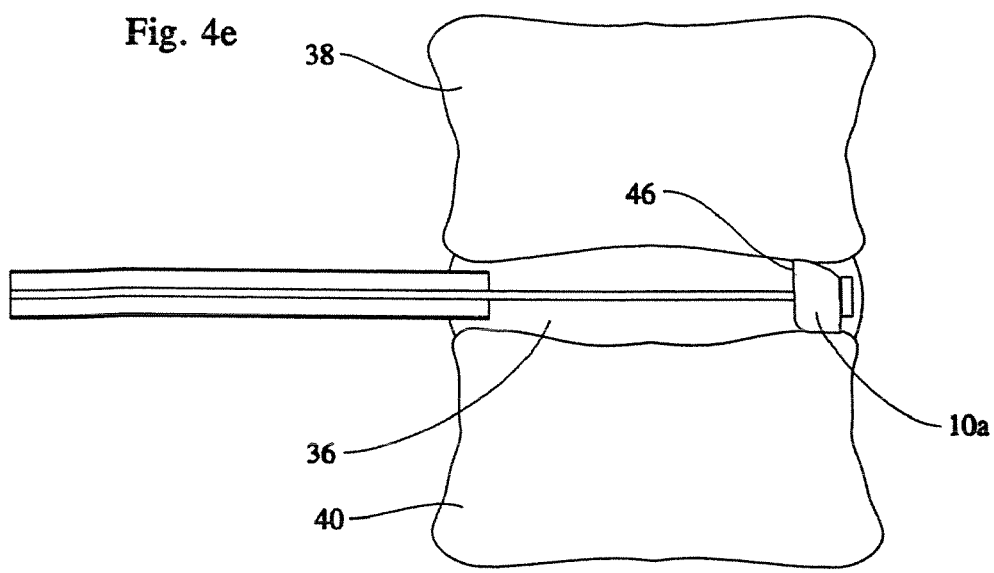
FIG. 4e is a side plan view of the rotatable component system of FIGS. 4a-d, showing the first rotatable component completely rotated to a final orientation.
Figure 4F:
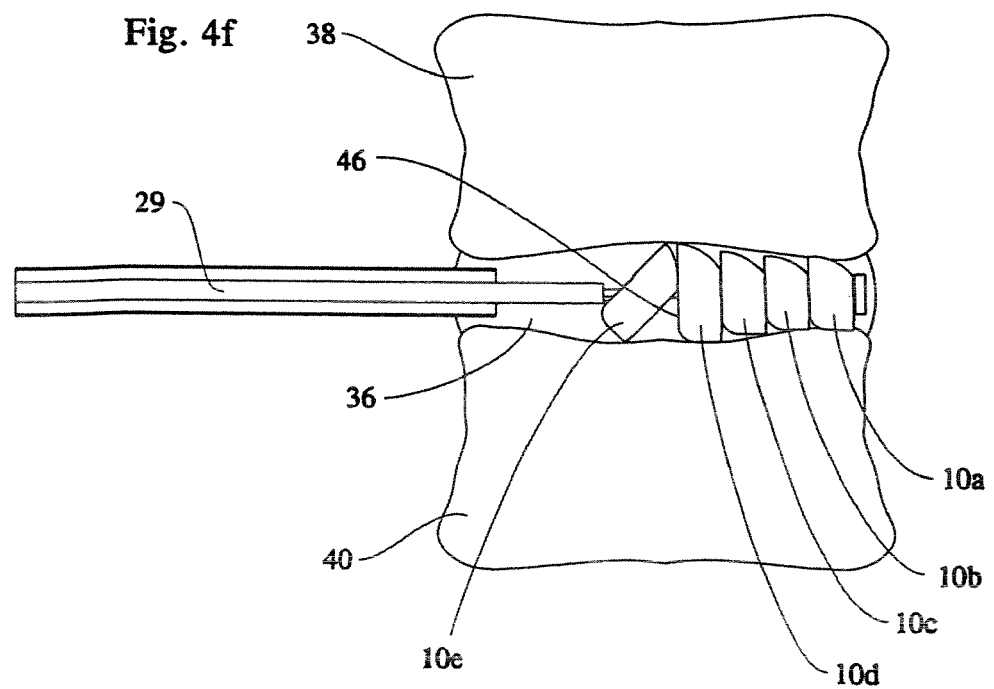
FIG. 4f is a side plan view of the rotatable component system of FIGS. 4a-e, showing a plurality of additional rotatable components successively advanced along the component guide and rotated into their final orientation, as well as a most-proximal of the visible rotatable components undergoing rotation after having made contact with the preceding rotatable component, and with the driving probe omitted for clarity.
Figure 4H:
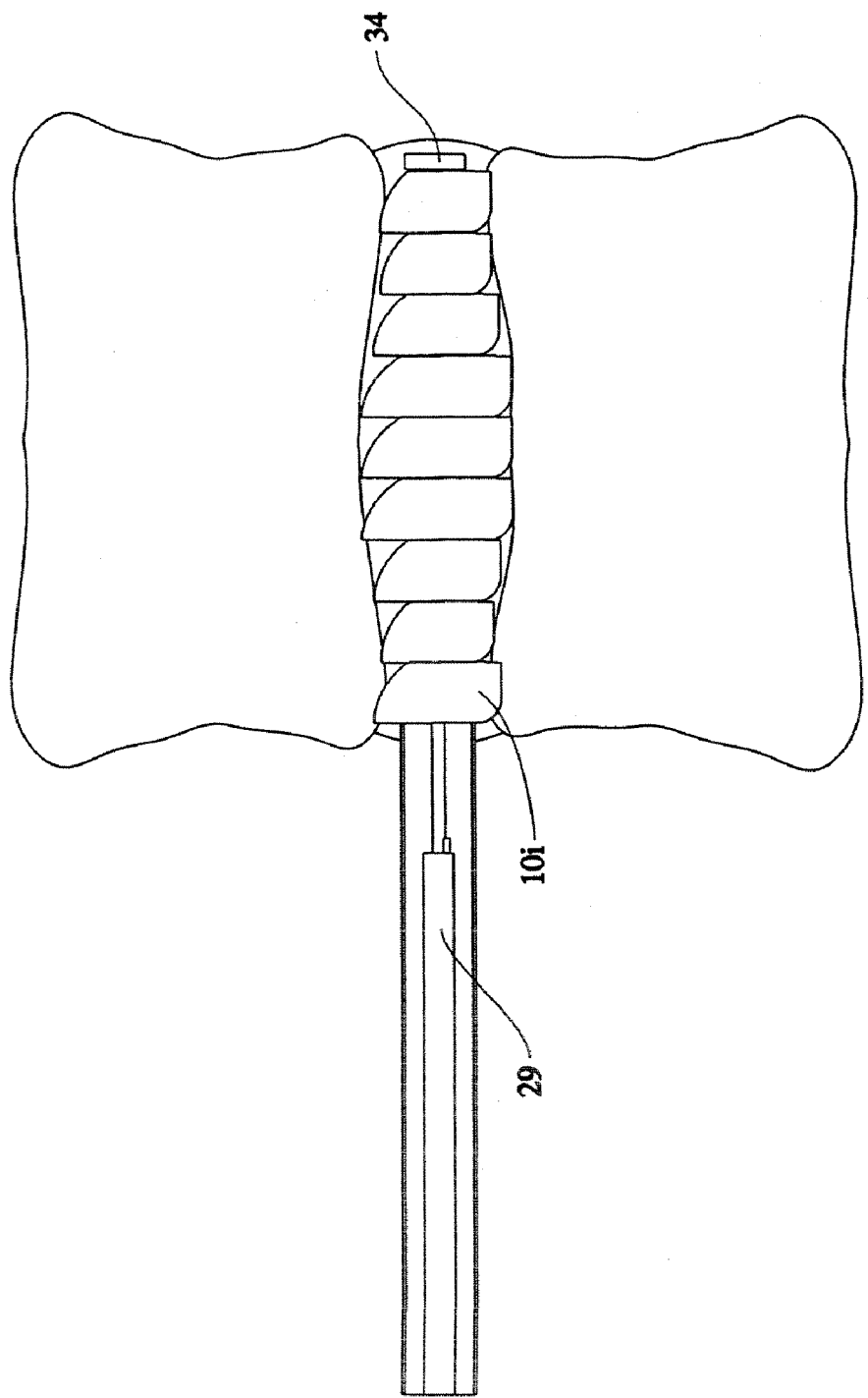
FIG. 4h is a side plan view of the rotatable component system of FIGS. 4a-g, showing a plurality of rotatable components substantially filling the cavity, and showing the driving probe being withdrawn through the delivery cannula.

Turning to FIGS. 4f, 4g, and 4h a plurality of additional rotatable components 10b, 10c, . . . , 10i are next successively advanced along the component guide 20. Upon initial contact with an exposed surface 46 of a preceding component, each new component making such initial contact rotates from a horizontal orientation to its final vertical orientation. Rotatable components 10 are continually added in this manner until the intervertebral space 36 is optimally filled by the components to whatever concentration of component occupancy is desired by the surgeon. The rotatable components 10a, 10b, . . . , 10i vary in vertical heights (i.e., have differing lengths—that is, distance from the distal end 12 to the proximal end 14) from one another to most effectively distract a tissue space such as the intervertebral space 36 without changing the size of the portal opening 32, and thereby obtain desired distraction in a tissue space such as the inter-body space.

It may be necessary to at least partially withdraw the delivery cannula 30 from the opening portal 32 while delivering the final rotatable component 10i.

Figure 4J:
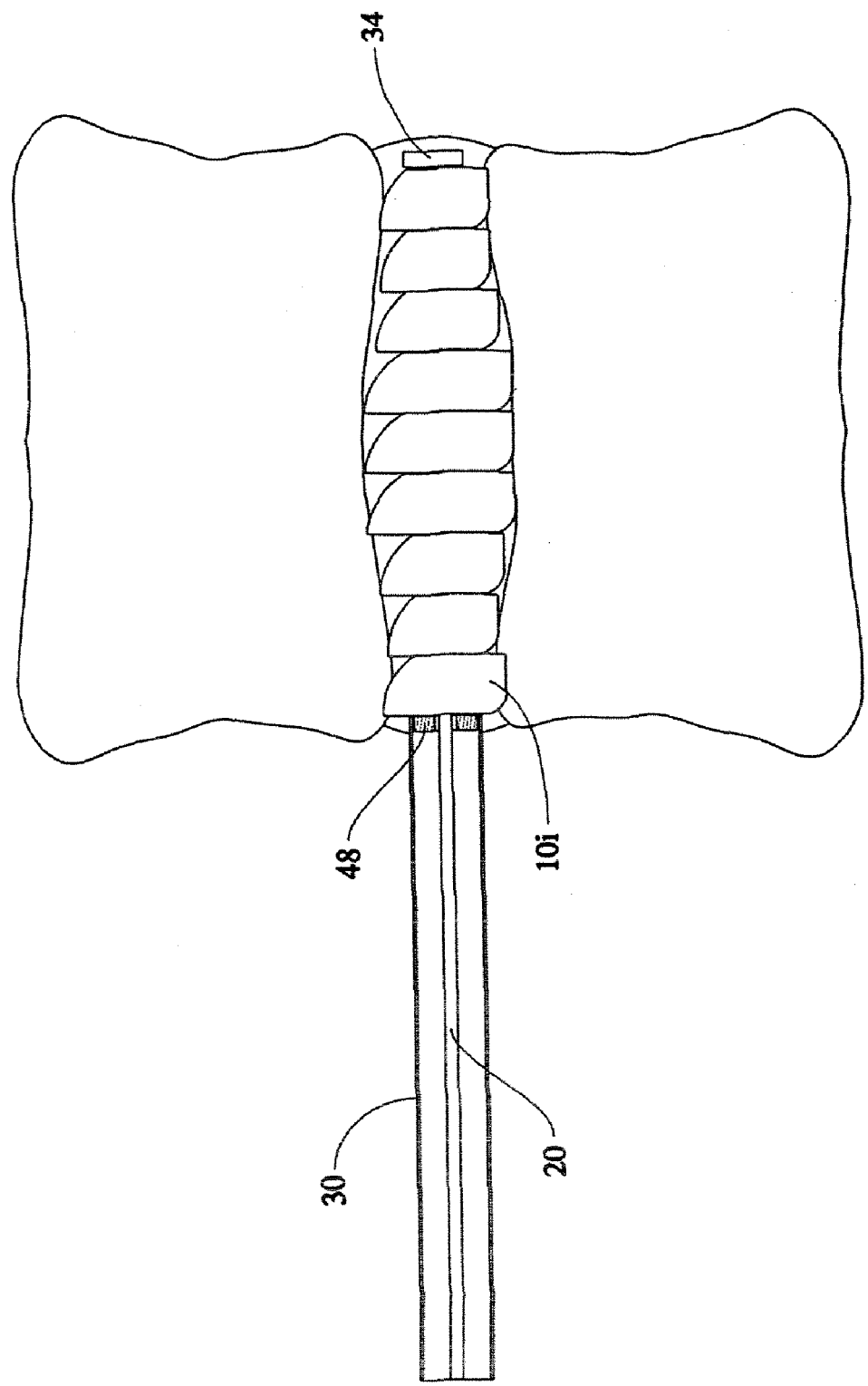
FIG. 4j is a side plan view of the rotatable component system of FIGS. 4a-i, showing the locking device (shown in cross-section) in its final position, immediately adjacent a most-proximal rotatable component.
Figure 5:
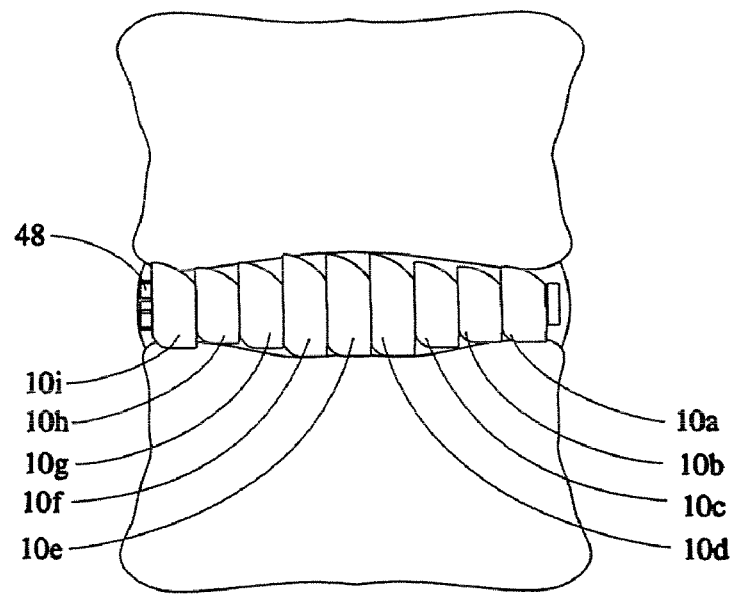
FIG. 5 is a side plan view of the rotatable component system of FIGS. 4a-k, after removal of the cannula and component guide.

After the last rotatable component 10i is rotated to its final, vertical orientation, the components 10a, 10b, . . . 10i might then preferably be tightened by pulling on the component guide 20, and tying the component guide 20 off at the exposed surface 46 of the last component 10i. Alternatively, after the component guide 20 is pulled, a lockable device 48 may first be delivered, via the delivery cannula 30 (as shown in FIGS. 4i-4j), to a position immediately adjacent the exposed surface 46 of the last component 10i, crimped off using a crimping tool 49 (as shown in FIG. 4k), and the component guide 20 may be tied off for yet additional integrity, and cut away. See FIG. 5. The locking device 48 could include a locking washer, threaded devices, bonded devices, or unidirectional devices, i.e. devices that can slide along the component guide in one direction, but cannot retreat in the opposite direction. The locking device 48 may be tapered in order to assist in alignment and frictionally lock together, resisting release prior to securing the locking device 48. The delivery cannula 30 is then completely removed, and the opening portal 32 is closed.

Figure 2:
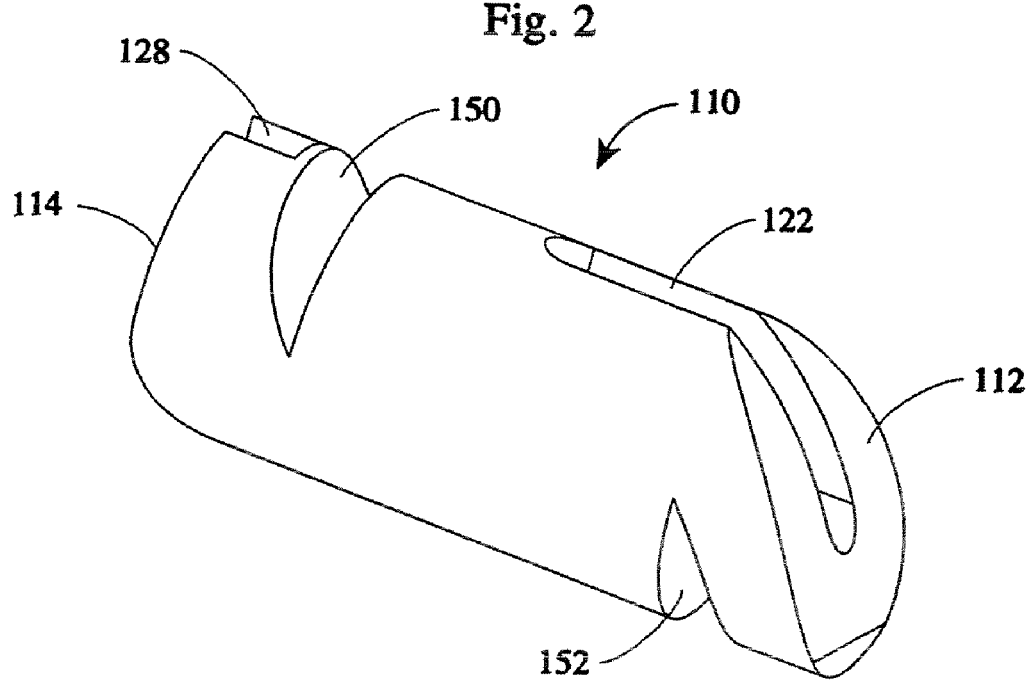
FIG. 2 is an enlarged perspective view of a second embodiment of a rotatable component of the present disclosure.
Figure 6:
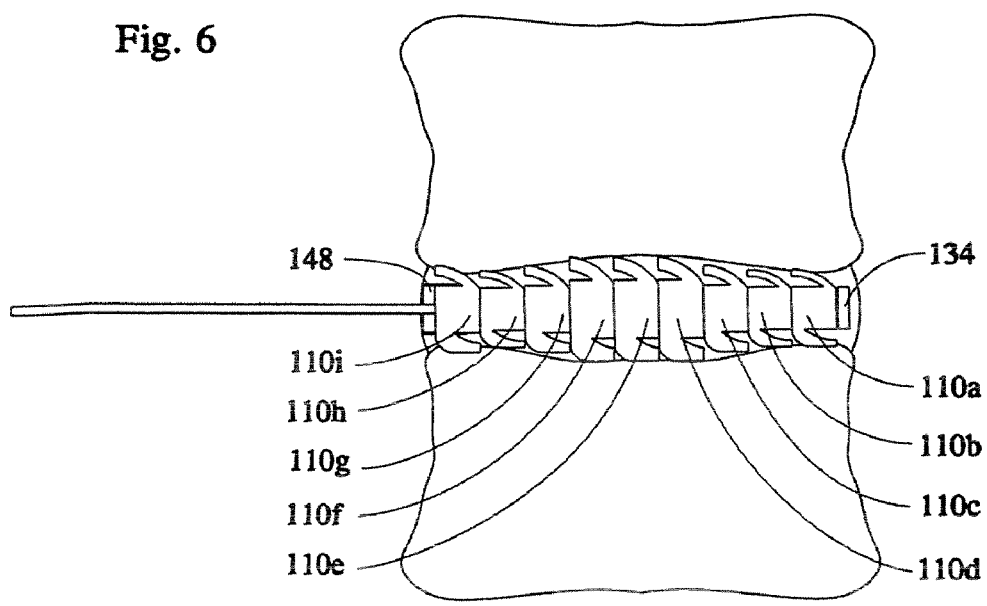
FIG. 6 is a side plan view of a rotatable component system of the present disclosure employing rotatable components of the type shown in FIG. 2.

Turning now to FIGS. 2 and 6, a rotatable component system employing an alternative embodiment of a component 110 is shown. In the description of this embodiment, like reference numerals to those reference numbers within the range of 1 thru 99, increased by 100, denote similar elements or features as the corresponding elements or features of such reference numerals identified in the first embodiment. Detailed descriptions of these elements or features are therefore omitted with respect to this embodiment, as unnecessarily duplicative. The rotatable components 110 include a relief, such as a notch or cavity 150, 152 spaced from the proximal end 114 and distal end 112, respectively. These cavities 150, 152 provide additional pressure (for fusion use) or flexibility (for nuclear replacement).

Figure 7:
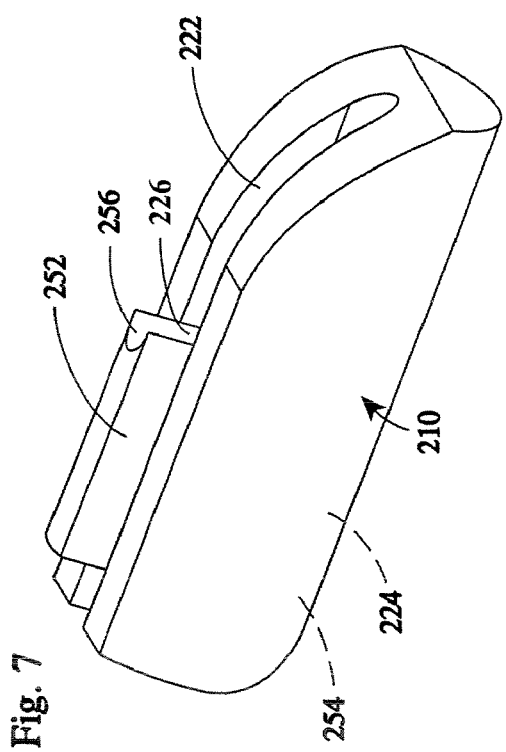
FIG. 7 is a perspective view of a rotatable component of a third embodiment of the present disclosure, including a male interlocking member.

Yet another embodiment of a rotatable component 210 is shown in FIG. 7. Like reference numerals, increased by 200, denote similar elements or features as the corresponding elements or features of such reference numerals identified in the first embodiment. The rotatable component 210 advantageously includes a male locking member 252 projecting from one side thereof. As the component 210 rotates from its horizontal orientation to its vertical orientation, upon contact with a preceding component 210 having a complementary female opening 254 therein, the male locking member 252 is securely received within the complementary female opening 254. As a result, the rotatable components 210 are locked together. The female opening 254 may be coextensive with the slot 224.

Figure 18A:
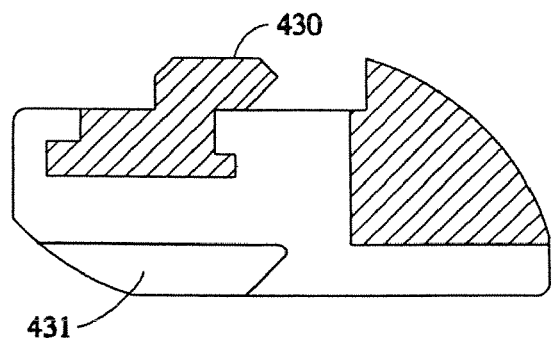
FIG. 18a is a cross-section taken along lines 18a-18a of FIG. 18c, and FIGS. 18b-c are top and side plan views of a male/female interlocking hook design.
Figure 18B:
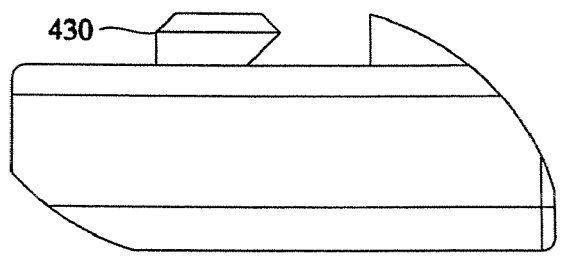
Figure 18C:
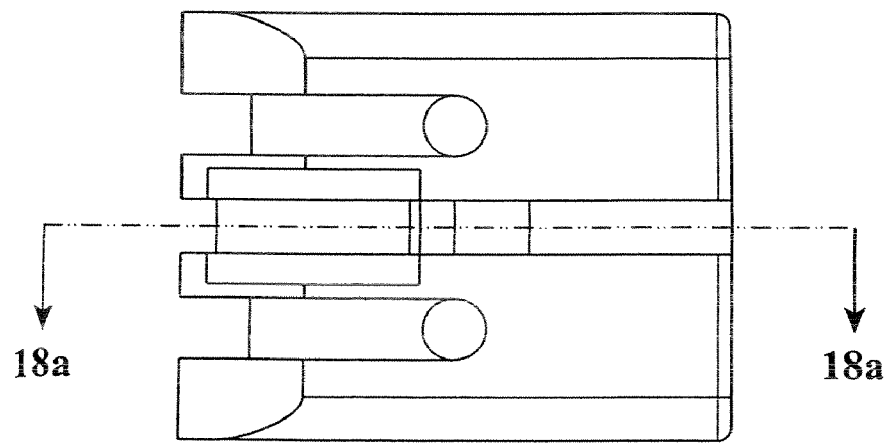

FIGS. 18a-c show a variation of the male/female locking rotating component described above. The male locking member might have a hook at the bottom 430 that would lock into a corresponding slot in the female member 431 of the adjoining component. This hook would provide further securing of the rotatable components to each other and would prevent the components from separating or further rotation once the desired rotation is complete.

In order to accommodate a component guide when the component 210 is fully rotated to its final vertical orientation, the male locking member 252 is provided with a component guide channel 256 therein, which is coaxial with the second hollow bore 226. The complementary female opening 254 may be a portion of, and contiguous with, the second slotted opening 224. By successively delivering yet additional similar rotatable components 210, of varying sizes, to a tissue space such as the intervertebral space, the intervertebral space may be substantially supported with interlocked rotatable components 210.

Figure 25A:
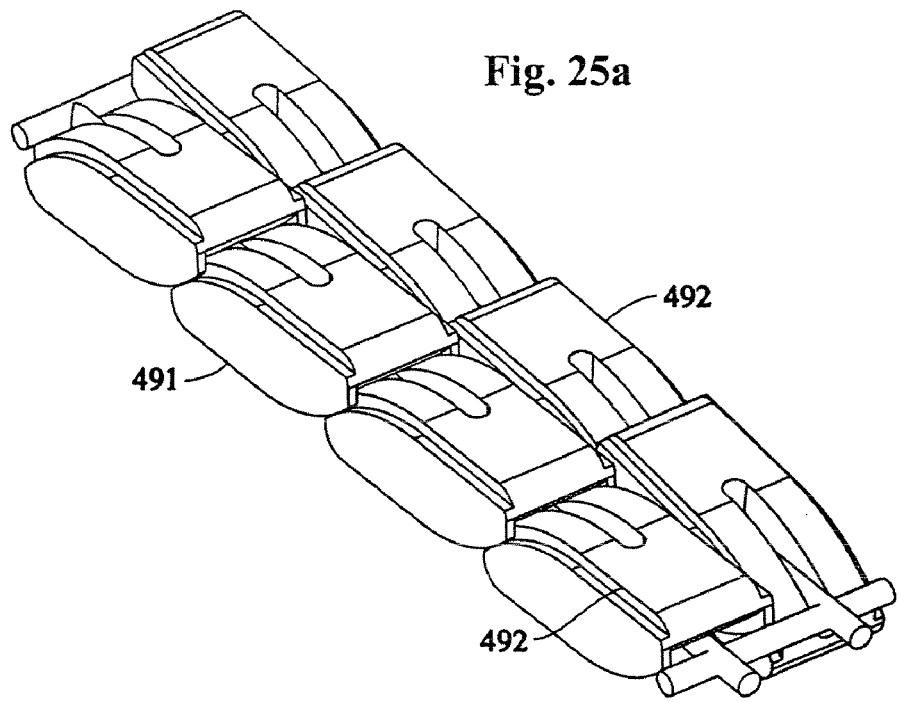
FIG. 25a is a perspective view of an alternate embodiment in which the components are delivered in two rows.
Figure 25B:
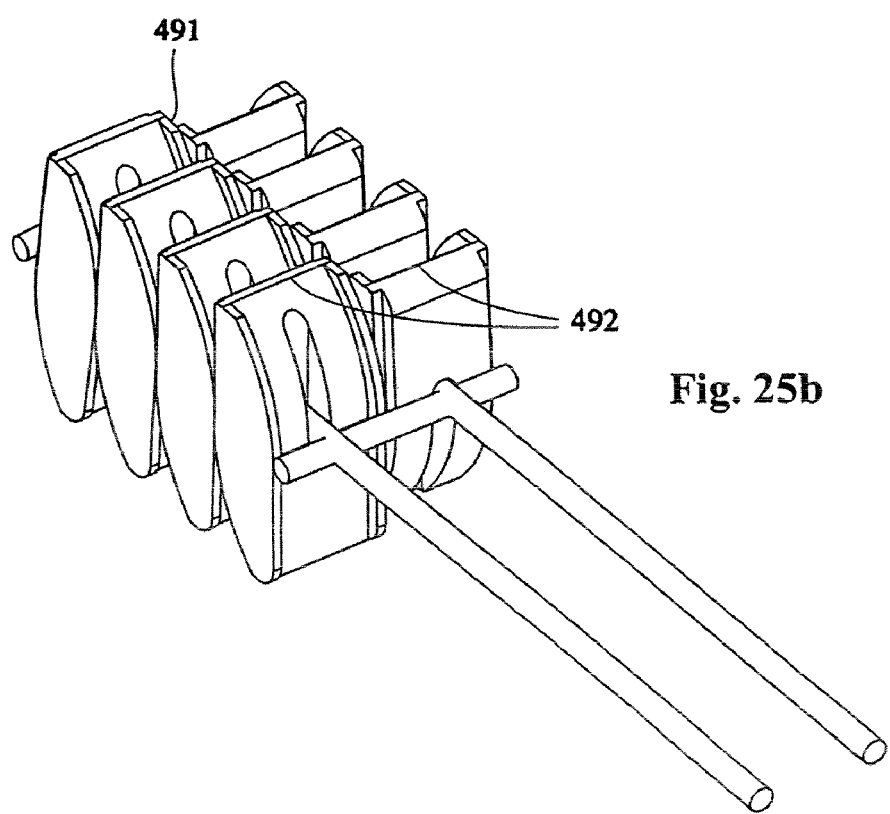
FIG. 25b is a perspective view of the embodiment shown in FIG. 7, and showing the components rotated to a second orientation.

In one variation of delivery as shown in FIGS. 25a and 25b the components might be delivered in two or more rows 481, 482 with the rotation of components in each row being in an opposite direction than the row of components next to it.

Figure 9:
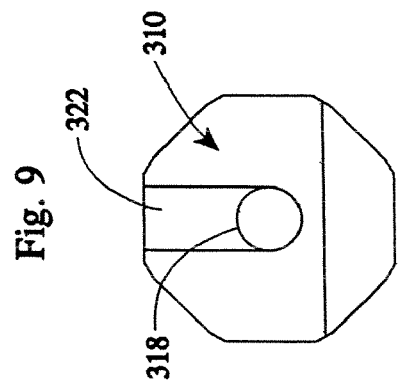
FIG. 9 is a distal end view of the rotatable component of FIG. 8.
Figure 8:
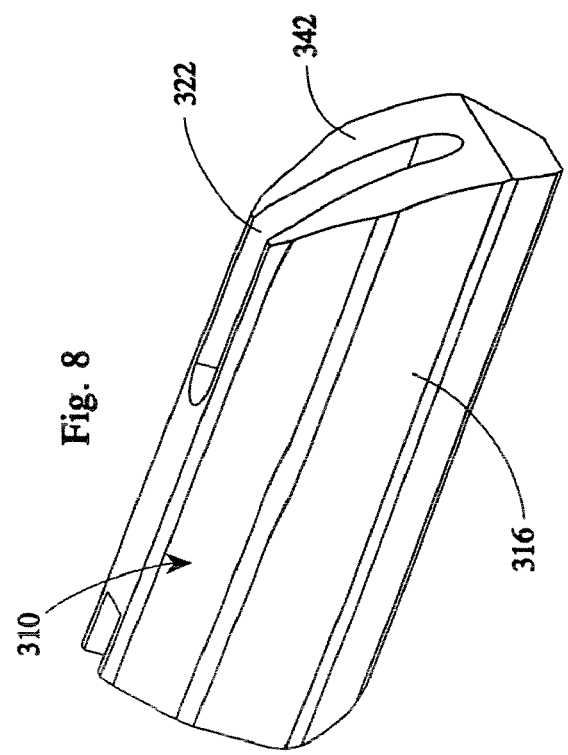
FIG. 8 is a perspective view of a rotatable component of the present disclosure demonstrating an alternative shape.
Figure 13:
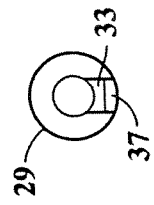
FIG. 13 is a distal end view of the driving probe of FIG. 10.
Figure 10:
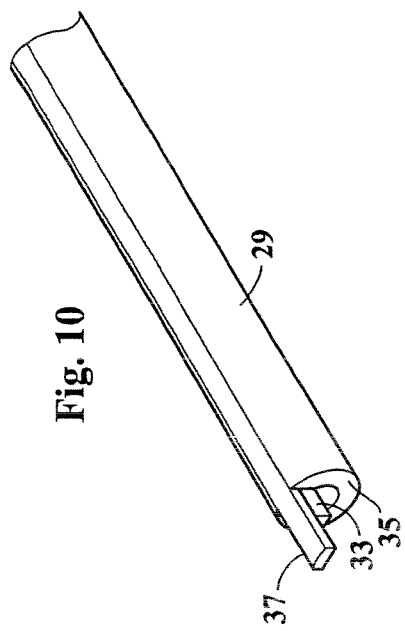
FIG. 10 is a perspective view of the driving probe of FIG. 4b.
Figure 11:
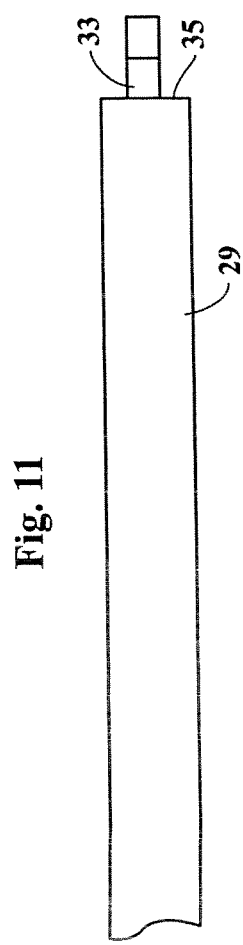
FIG. 11 is a top plan view of the driving probe of FIG. 10.
Figure 12:
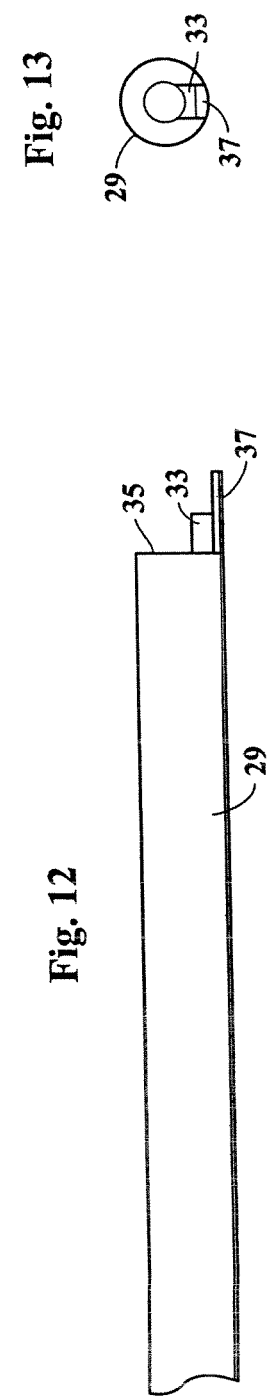
FIG. 12 is a front plan view of the driving probe of FIG. 10.

Turning to FIGS. 8 and 9, a rotatable component 310 is shown having an octagonal cross-sectional shape. Like reference numerals, increased by 300, denote similar elements or features as the corresponding elements or features of such reference numerals identified in the first embodiment. Notwithstanding the flat sides of the main body 316, the rotatable component 310 is provided with a curved leading surface 342 to facilitate rotation of the component 310 upon contact with a dead-man or with a preceding component during delivery into an intervertebral space.

Figure 17A:
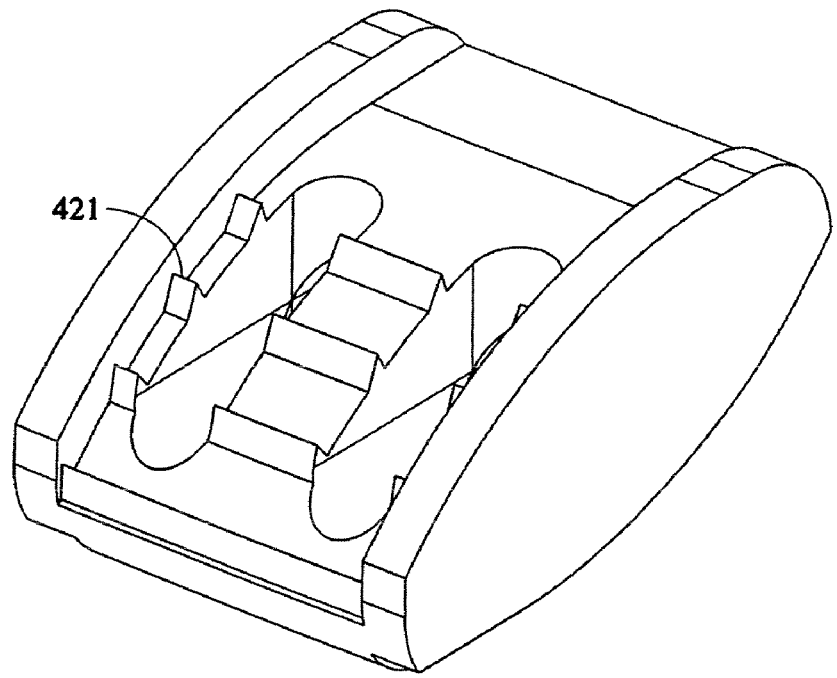
FIGS. 17a and 17b are two perspective views of a rotating component with ratcheting capabilities.
Figure 17B:
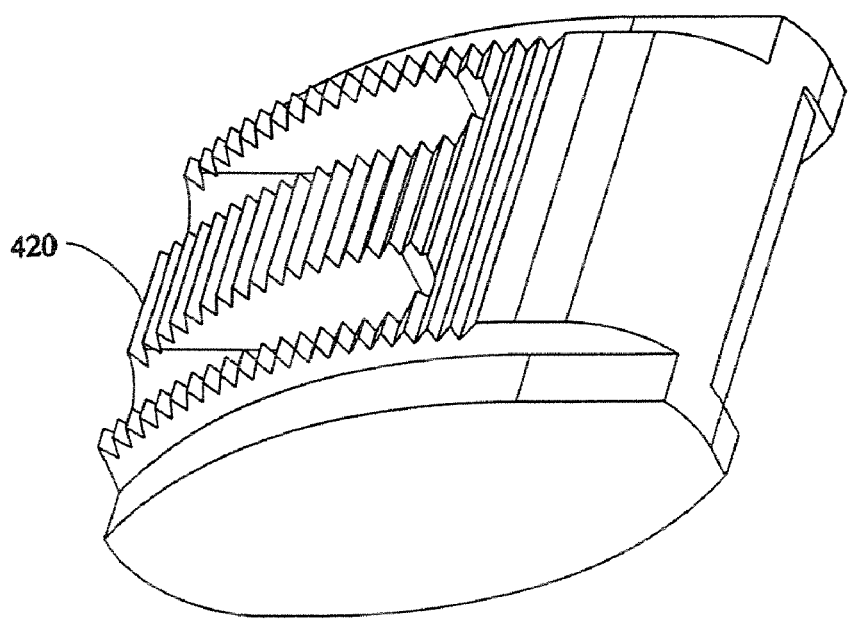

In one variation, shown in FIGS. 17a and 17b, the components could include ratcheting teeth 420 to facilitate precise rotation. The ratcheting teeth 420 would lock into the adjacent component ratcheting teeth 421. This variation would allow for rotation where desired and would also provide further interlocking stability for fully rotated components.

Figure 21A:
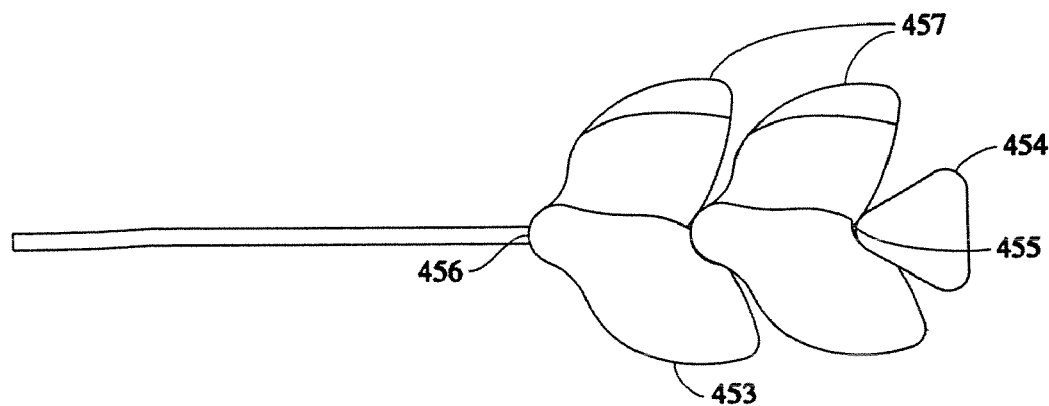
Figure 21B:
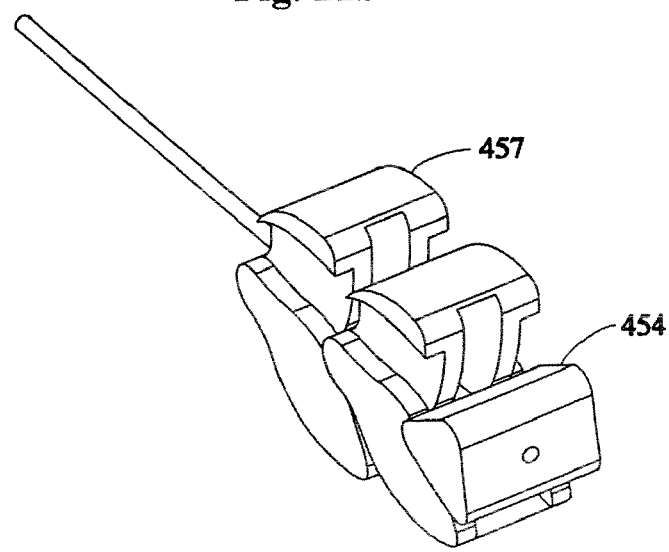

In one variation the components are made up of sub-assemblies of a first and second region, or bottom and top piece, which are connected to each other by a hinged mechanism 451, as shown in FIGS. 20a-d, and are delivered in a first orientation, e.g. horizontally, together in a closed position 452. The top and bottom face of the bottom and top components respectively consists of arced surfaces 453 which are eccentric relative to the hinged axis 451 such as a cam. As shown in FIGS. 21a and 21b the component guide is terminated at the distal end with a dead man 454 which is positioned tangent to the arced faces of both the top and bottom components 455. The geometry of the proximal tail of each component 456 is similar to that of the dead man 454. After delivery of the one or more components, a force is applied to the proximal tail of the last component 456, which causes all the components to rotate vertically about their hinge axis to an open position 457 thereby distracting the desired tissue such as vertebral endplates. This would allow, for example, the distraction to occur without translational movement of the endplates relative to each other.

Figure 14:
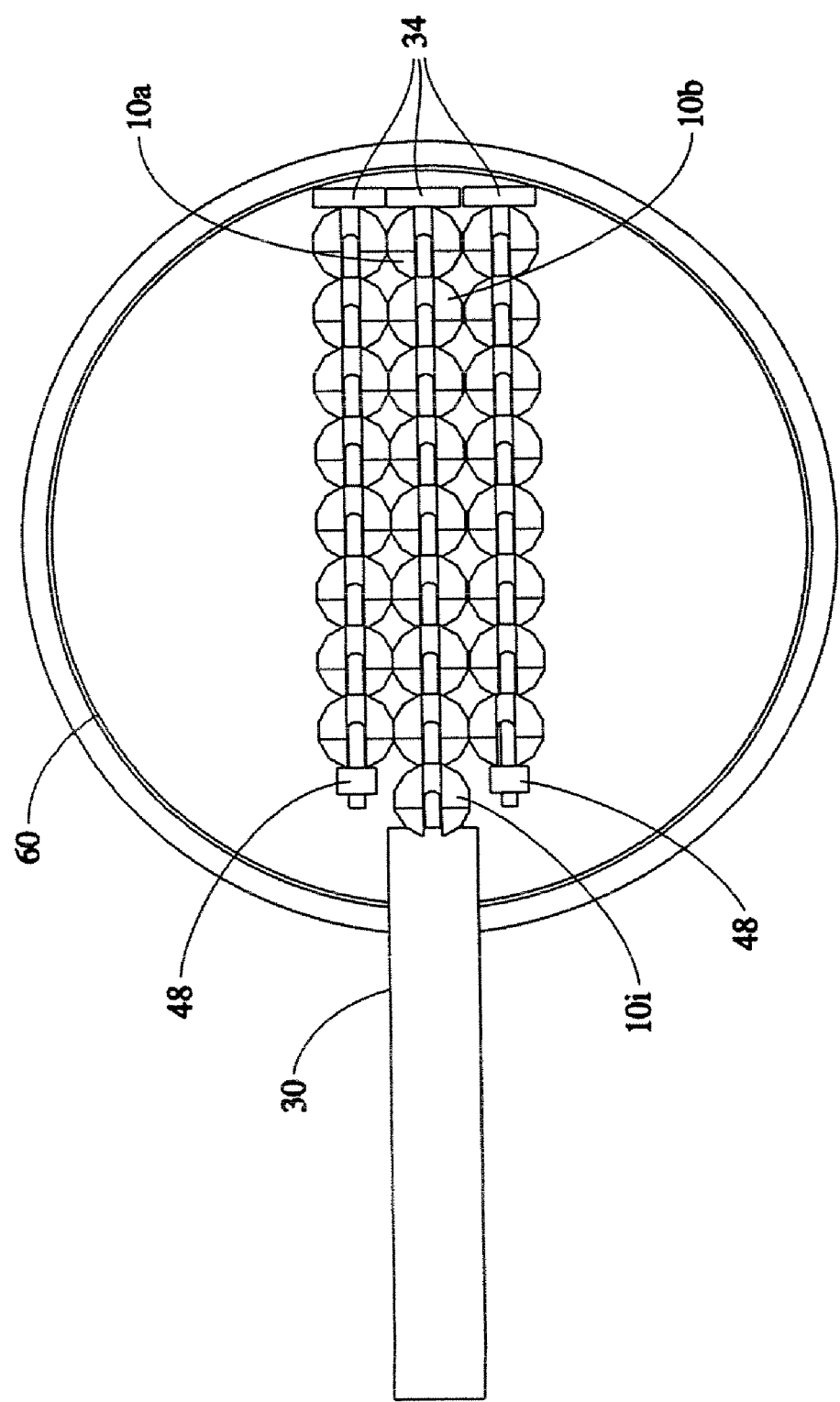
FIG. 14 is a side plan view of an implantation utilizing an rotatable component system of the present disclosure, wherein rotatable components are delivered, rotated, and stacked into rows and columns.

As shown in FIGS. 14 and 15, the rotatable segments 10 may be delivered in a variety of stackable formations. In some applications only one rotatable component may be desired. For instance, the rotatable segments 10a, 10b, ..., 10i, ... may be delivered to form an arrangement of rotatable segments in an array of rows and columns, such as in FIG. 14, to thereby support a specific area of the adjacent endplates 60. Each row of rotatable segments 10 may be led by a dead-man 34 and capped or closed by a locking device 48. Alte atively, the component guide 20 may be fed to form a shaped track, such as in the form of a 360° arc, which the rotatable segments 10a, 10b, 10w follow as they are delivered and rotated to their final orientation, as shown in FIG. 15. The segments 10a, 10b, ..., 10w of FIG. 15 encapsulate a biologic device, for example a sponge, BMP, or other types of growth materials.

Figure 19A:
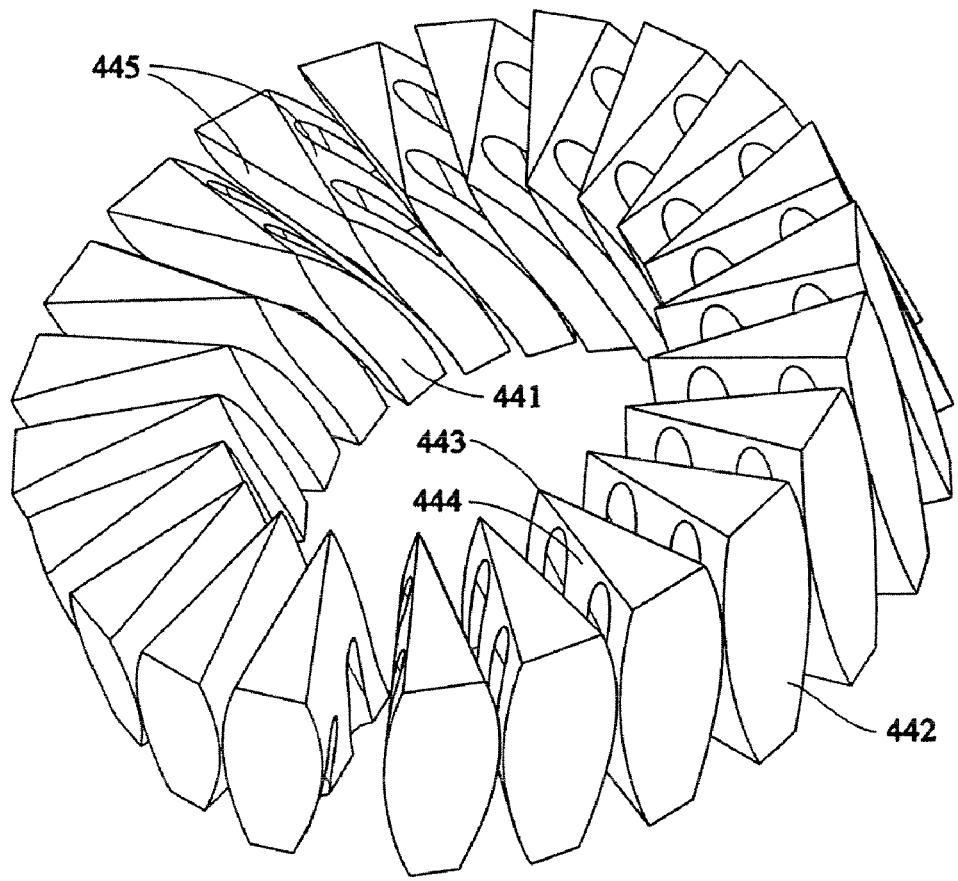
FIGS. 19a and 19b are two perspective views of an arc creating components.
Figure 19B:
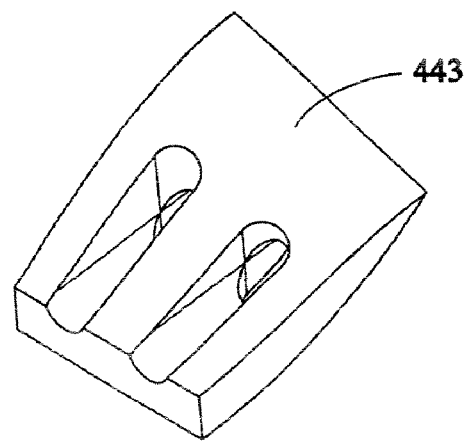
Figure 20A:
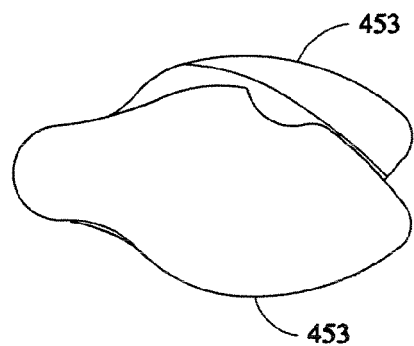
FIGS. 20a-d and 21a-b are various perspective views of an alternative embodiment of the rotatable components of the present disclosure.
Figure 20B:
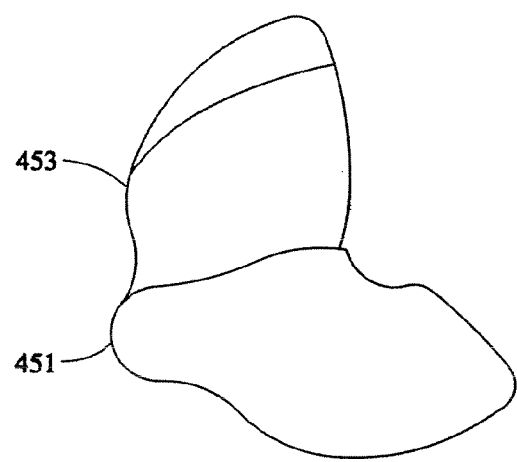
Figure 20C:
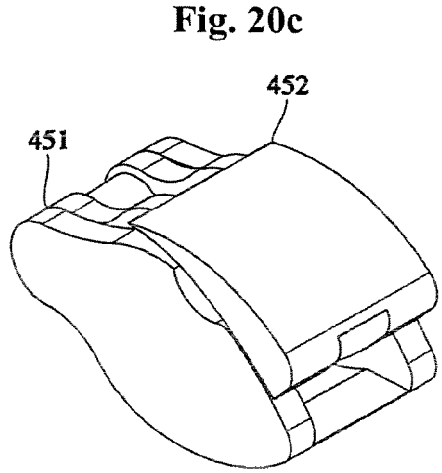
Figure 20D:
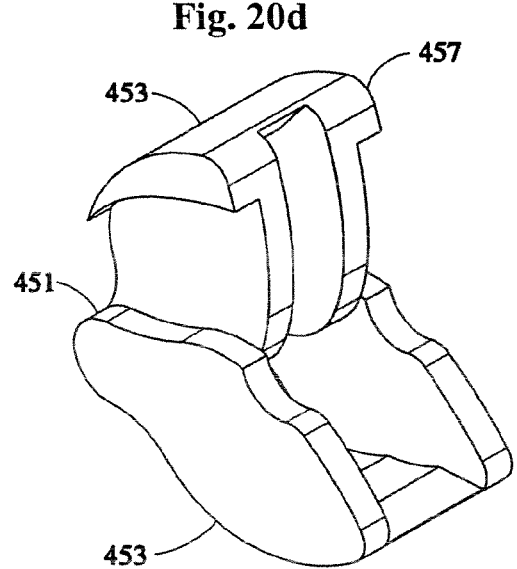

In one variation, shown in FIG. 19a, an arc of 360 degrees or less could be constructed with the use of a component where the inner all of the segment 441 is narrower than the outer wall 442, for example, forming a wedge shape. The ratio of the thickness of the inner and outer wall would determine the radius of the arc. In one variation, the one or both faces of the component might be a helical-like surface which facilitates two axes of rotation 443. As the bottom face of a component articulates against the top face of an adjacent component, the initial component is forced to rotate simultaneously up about its wide axis, as well as inward about its long axis, to form an arc.

Figure 24A:
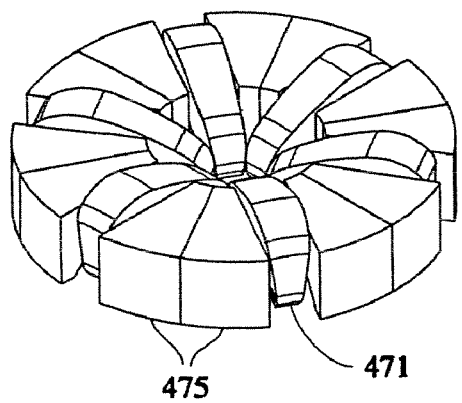
Figure 24B:
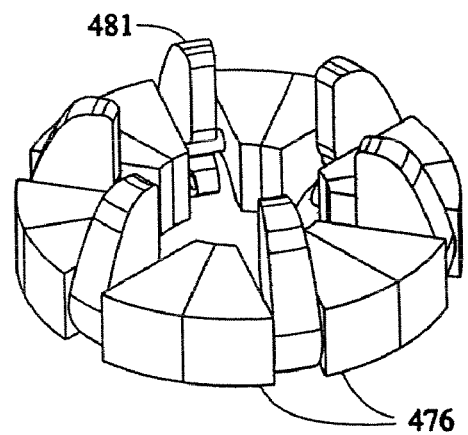
Figure 24C:
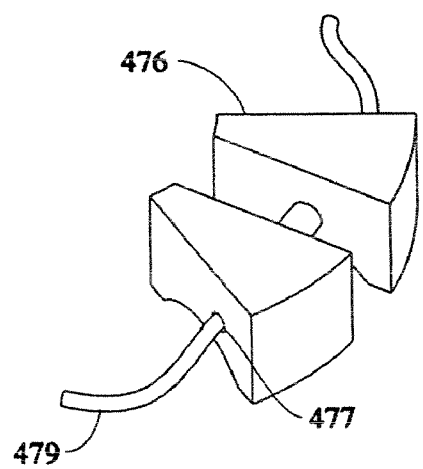
Figure 26:
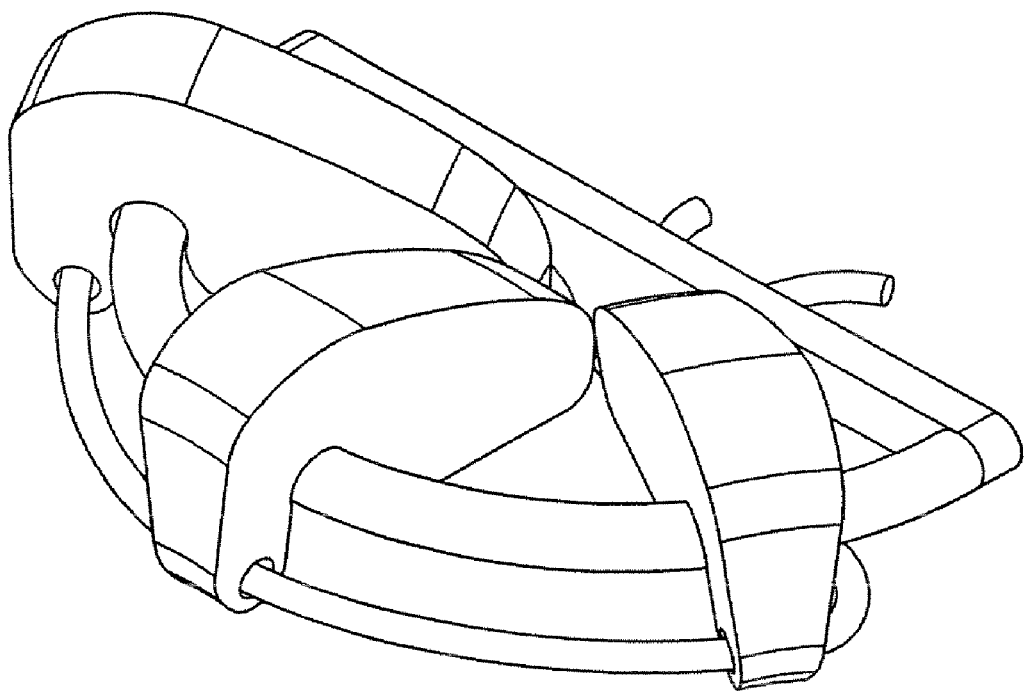
FIG. 26 is a perspective view of yet another embodiment, wherein segments are disposed along a D-shaped ring.

In one variation, shown in FIGS. 23a-d, the rotatable components 471 would be delivered into the cavity and horizontally assembled onto a ring 472 within a tissue cavity space such as an interbody space. Due to size efficiency requirements, six rotatable components might be preferred, although more or less could be utilized. The rotatable components might be configured with a precise relief 473 so that they could be snapped onto the ring within the cavity space. To maintain location on the ring, the diameter of the ring might be slightly smaller 474 at the location of each snapped on rotating component 471. In a further alternative version, as shown in FIGS. 24a-c, spacers 475 might be placed between the rotatable components 471 to constrain the position of the components relative to the ring. In yet another version, the ring might be comprised of a number of spacing components 476 which may be equal to the number of rotatable components 471. These spacing components might be delivered with an independent component guide so they could be assembled into a ring within the cavity space. The rotatable components then could be delivered, attached to the ring, and then rotated to a vertical position. The spacing components might be delivered together with the rotatable components prior to delivery. The spacing components might have an interlocking male/female mechanism between the components to enhance stability. In either event separate tensioning component guides, for example, such as suture, are then passed respectively through a hole 477 in the spacing components and through a separate hole 478 of the rotatable components as they are delivered into the cavity. Once delivered the tensioning component guide 479 passing through the spacing components is tensioned followed by the tensioning 480 of the rotatable components causing the components to become locked relative to each other and inducing rotation of the rotatable components respectively. As shown in FIG. 26 the shape of the ring could be a D shape. It could also be an oval or any other shape to accomplish the desired medical result. The shape might also be an arc that is less than an enclosed circle such as for example, a C shape. In all versions upon completion of the assembly the components would be tensioned and forced into a vertical position 481 resulting in the distraction of the adjacent tissue such as the vertebral endplates.

It is recognized that the rotatable component systems disclosed herein may be used as permanent implants and/or instruments for temporary distraction, such as to permit other procedures to take place within the intervertebral space. Where distraction is desired temporarily, an instrument made in accordance with the present disclosure may be employed. Once other procedures requiring temporary distraction are conducted, the instrument is removed.

While several embodiments have been described herein, it will be understood that variations may be made without departing from the scope of the present disclosure.

I claim:

1. A medical device comprising:
a component guide comprising a slidable elongated material;
at least one linkable segment, which slides over the component guide, the component guide passing through each of the at least one linkable segments, each of the at least one linkable segments having a length, a width that is shorter than the length, a distal end, a proximal end located opposite the distal end along the length, and a first hollow bore receiving the component guide, said first hollow bore extending the length of the linkable segment from the proximal end to the distal end, and said at least one linkable segment further including a first slotted opening and a second slotted opening, each of said first and second slotted openings being contiguous with the first hollow bore and with a second hollow bore extending the width of the linkable segment at an angle perpendicular to and offset from the first hollow bore and intersecting the first hollow bore, the first slotted opening extending along the length of the linkable segment on a first side of the first hollow bore from the proximal end to the second hollow bore, and said second slotted opening extending along the length of the linkable segment on a second side of the first hollow bore from the second hollow bore to the distal end, the first and second slotted openings to facilitate rotation of the linkable segment from a first orientation relative to the component guide, wherein the component guide is coaxially aligned with the first hollow bore, to a second orientation relative to the component guide, wherein the component guide is coaxially aligned with the second hollow bore.

2. The medical device of claim 1, further comprising at least one additional linkable segment engaged with the component guide, the additional linkable segment having a distal end, a proximal end, and a first hollow bore therethrough to receive the component guide, said at least one additional linkable segment further including a first slotted opening and a second slotted opening, each of said first and second slotted openings being contiguous with the first hollow bore and with a second hollow bore extending perpendicularly to the first hollow bore, the first slotted opening extending on a first side of the first hollow bore from the proximal end to the second hollow bore, and said second slotted opening extending on a second side of the first hollow bore from the second hollow bore to the distal end to facilitate rotation of the additional linkable segment from a first orientation relative to the component guide, wherein the component guide is coaxially aligned with the first hollow bore, to a second orientation relative to the component guide, wherein the component guide is coaxially aligned with the second hollow bore.

3. The medical device of claim 1, further comprising:
a stop member attached to the distal end of the component guide, the at least one linkable segment including an arcuate proximal surface to initiate rotation from the first orientation to the second orientation subsequent to contact of the distal end of the most distal linkable segment on the component guide and the stop member.

4. The medical device of claim 1, in combination with a probe for urging each of the at least one linkable segments toward a desired location along the component guide.

5. The combination of the medical device and probe of claim 4, wherein the probe includes a retractable protrusion for selectively engaging a relief provided in the at least one linkable segment, said retractable protrusion preventing rotation of the linkable segment away from the first orientation when engaged with the relief.

6. The medical device of claim 1, wherein the distal end of each of the at least one linkable segment is curved to facilitate rotation of the respective linkable segment upon one of contact with one of another linkable segment or a stop member provided at a distal end of the component guide, or tightening of a tensioning member passing through each of the plurality of linkable segments, said tensioning member being separate from the component guide.

7. The medical device of claim 1, wherein the first slotted opening and the second slotted opening are disposed in a mirrored arrangement to one another with respect to a diagonal plane bisecting the at least one linkable segment.

8. The medical device of claim 1, wherein the first elongate slot is open above an axis extending from the distal end of the at least one linkable segment to the proximal end of the at least one linkable segment, and the second elongate slot is open below the axis extending from the distal end of the at least one linkable segment to the proximal end of that one linkable segment.

9. The medical device of claim 1, wherein the component guide is disposed in a substantially straight orientation.

10. The medical device of claim 1, wherein the component guide is disposed in a curved orientation.

11. The medical device of claim 10, wherein the component guide is disposed in one of a substantially circular orientation, a D-shaped orientation, or a C-shaped orientation.

12. The medical device of claim 1, wherein the second orientation is substantially perpendicular to the first orientation.

13. The medical device of claim 2, wherein each of the linkable segments, in its first orientation, is tapered from a relatively wider thickness on a first side of the component guide to a relatively narrower thickness on a second side of the component guide, to facilitate rotation of the linkable segment from the first orientation to the second orientation.

* * * * *